United States Patent
Ramamurthy et al.

(10) Patent No.: US 12,017,093 B2
(45) Date of Patent: Jun. 25, 2024

(54) METHODS AND SYSTEMS FOR CONFIRMING FOCUS OF ULTRASOUND BEAMS

(71) Applicant: Cordance Medical Inc., Mountain View, CA (US)

(72) Inventors: Bhaskar S. Ramamurthy, Los Altos, CA (US); Mallika Keralapura, San Jose, CA (US); John Douglas Marshall, Los Gatos, CA (US)

(73) Assignee: Cordance Medical Inc., Mountain View, CA (US)

( * ) Notice: Subject to any disclaimer, the term of this patent is extended or adjusted under 35 U.S.C. 154(b) by 0 days.

(21) Appl. No.: 18/358,295

(22) Filed: Jul. 25, 2023

(65) Prior Publication Data

US 2024/0033541 A1    Feb. 1, 2024

Related U.S. Application Data

(60) Provisional application No. 63/393,388, filed on Jul. 29, 2022.

(51) Int. Cl.
*A61N 7/00*    (2006.01)

(52) U.S. Cl.
CPC ........ *A61N 7/00* (2013.01); *A61N 2007/0026* (2013.01); *A61N 2007/0039* (2013.01);
(Continued)

(58) Field of Classification Search
None
See application file for complete search history.

(56) References Cited

U.S. PATENT DOCUMENTS

| | | | |
|---|---|---|---|
| 2009/0088623 A1* | 4/2009 | Vortman | A61B 8/5276 601/3 |
| 2014/0135681 A1* | 5/2014 | Angelsen | A61N 7/00 604/22 |

(Continued)

FOREIGN PATENT DOCUMENTS

| | | |
|---|---|---|
| WO | 2021176275 A1 | 9/2021 |
| WO | 2022032283 A2 | 2/2022 |

OTHER PUBLICATIONS

Application No. PCT/US2023/028659, International Search Report and Written Opinion, dated Nov. 16, 2023, 11 pages.

*Primary Examiner* — Joel Lamprecht
*Assistant Examiner* — Ashish S Jasani
(74) *Attorney, Agent, or Firm* — Kilpatrick Townsend & Stockton LLP

(57) ABSTRACT

Methods and systems confirm the treatment focus location of ultrasound energy to be delivered to a patient from a plurality of transducers. The location of focus of treatment ultrasound may be confirmed prior to the start of ultrasound therapy. In some embodiments, ultrasound therapy may comprise delivering treatment ultrasound energy from the treatment ultrasound transducers through the skull to the brain of a patient. Methods for confirming the treatment ultrasound focus location comprise determining receive focus profiles $\phi_{x,v_i}$ for particular candidate three-dimensional (3D) treatment focus locations and particular assumed ultrasound propagation velocity profiles; performing a pre-treatment (e.g. low-power) ultrasound transmission into the brain of the patient; receiving return signals; and determining the location of treatment focus based at least in part on the received return signals and the receive focus profiles $\phi_{x,v_i}$.

20 Claims, 5 Drawing Sheets

(52) U.S. Cl.
CPC ............ *A61N 2007/0052* (2013.01); *A61N 2007/0078* (2013.01)

(56) References Cited

U.S. PATENT DOCUMENTS

| | | |
|---|---|---|
| 2016/0007960 A1 | 1/2016 | Son et al. |
| 2019/0129026 A1* | 5/2019 | Sumi ................... G01S 7/52038 |
| 2019/0175954 A1 | 6/2019 | Levy et al. |
| 2019/0183457 A1 | 6/2019 | Ramamurthy |
| 2019/0184204 A1* | 6/2019 | Ramamurthy ....... A61B 8/5207 |
| 2019/0308038 A1 | 10/2019 | Prus et al. |
| 2020/0107811 A1* | 4/2020 | Sutton ................. A61B 8/0808 |
| 2023/0082109 A1 | 3/2023 | Ramamurthy et al. |

* cited by examiner

METHODS AND SYSTEMS FOR CONFIRMING FOCUS OF ULTRASOUND BEAMS

REFERENCE TO RELATED APPLICATIONS

This application claims priority from, and for the purpose of the United States the benefit under 35 USC 119 in relation to, U.S. application No. 63/393,388 filed 29 Jul. 2022, which is hereby incorporated herein by reference.

FIELD

This invention relates to methods and systems that apply focused ultrasound to brain tissue as part of a therapeutic treatment.

BACKGROUND

Drugs are an important treatment modality for a range of diseases affecting the brain including brain cancers. Treatment of diseases of the brain is challenging in part due to the structure of the blood brain barrier. The blood brain barrier separates circulating blood from other brain tissue, and has a highly selective permeability. This barrier prevents about 98% of small molecules and nearly 100% of large molecules from entering the brain from the bloodstream. This makes it difficult to transport drugs to various tissues of the brain, e.g. to tumor sites.

The blood brain barrier can be caused to open in certain regions by delivering ultrasound to those regions in the presence of microbubbles, thereby increasing the possibility for a wider range of molecules of different sizes to pass from the bloodstream into tissues of the brain. This technique may be applied to allow drugs to be delivered to the brain. Targeted ultrasound can selectively and transiently open the blood brain barrier, as taught for example in the Patent Cooperation Treaty (PCT) application published under WO2018/026738, which is hereby incorporated herein by reference.

The techniques disclosed in PCT publications No. WO2018/026738 and WO2021/154730 involve the use of a cap or helmet structure that includes a transducer assembly comprising a plurality of ultrasound transducers which are placed on the head of a patient. The ultrasound transducer assembly may comprise a number of imaging transducer elements adapted for ultrasound imaging, a number of treatment transducer elements for delivering treatment ultrasound energy to the brain of the patient.

Where the peak negative pressure (i.e. the maximum amplitude negative pressure) caused by the application of treatment ultrasound is greater than a threshold level in the presence of microbubbles, the blood brain barrier will open. The peak negative pressure is typically greatest at the location of focus of the treatment ultrasound energy from the treatment transducer elements. Consequently, there is a desirability to confirm the location of focus (also referred to herein as the focus location or simply as the focus, for brevity) of treatment ultrasound energy. There is a further desire to confirm the focus location prior to administering the treatment ultrasound energy to a subject.

In traditional diagnostic imaging for anatomical structures other than the brain (e.g. the liver), ultrasound images can be obtained. Thus, at least a visual confirmation of the location of the focus of the treatment ultrasound beams can be obtained by ultrasound imaging. The brain, however, is difficult to image with ultrasound, thus making it challenging to use ultrasound imaging to confirm the location of focus of ultrasound treatment. There at least two challenges which make it difficult to confirm the focus location for ultrasound treatment using ultrasound imaging. Firstly, the human skull is a thick anatomical structure and is difficult to obtain ultrasound images through the skull. Secondly, it is challenging to ascertain the speed of sound in the skull of a live human patient with precision.

There remains a desire to reliably confirm the treatment focus location of ultrasound energy from a plurality of treatment transducer elements located in a cap or similar structure adjacent to the head of a patient. There is a related desire to confirm this treatment ultrasound focal location prior to administration of treatment ultrasound energy suitable to open one or more regions of the blood brain barrier and/or suitable for other therapeutic treatments (e.g. ultrasound ablation, ultrasound neuromodulation and/or the like).

SUMMARY

This invention has a number of aspects that may be applied together, individually and in any sub-combination. These include, without limitation:
  Methods and systems for confirming the focus of ultrasound in the blood brain barrier of a patient; and
  Methods and systems for delivering ultrasound to a patient.

One aspect provides a method for confirming a treatment characteristic of an ultrasound therapy system. The ultrasound therapy system may comprise a plurality of transmit transducers for transmitting ultrasound energy into the brain of a patient and a plurality of receive transducers for receiving reflected ultrasound energy from the brain of the patient. The method may comprise obtaining a proposed ultrasound treatment parameterized by, for each of the plurality of transmit transducers, treatment values for a corresponding plurality of transmission parameters. The method may also comprise transmitting pre-treatment ultrasound energy into the brain of the patient. Transmitting the pre-treatment ultrasound energy may comprise causing each of the plurality of transmit transducers to transmit ultrasound energy according to pre-treatment values for the corresponding plurality of transmission parameters. The pre-treatment values for a first one or more of the corresponding plurality of transmission parameters may be different than the treatment values for the first one or more of the corresponding plurality of transmission parameters and the pre-treatment values for a second one or more of the corresponding plurality of transmission parameters may be the same as the treatment values for the second one or more of the corresponding plurality of transmission parameters. The method may also comprise receiving return pre-treatment signals at the plurality of receive transducers. The method may also comprise determining the treatment characteristic based at least in part on the received return pre-treatment signals.

The treatment characteristic may be a treatment focus location of the proposed ultrasound treatment.

The first one or more of the corresponding plurality of transmission parameters may be one of the corresponding plurality of transmission parameters.

The first one or more of the corresponding plurality of transmission parameters may comprise a power of the ultrasound transmission by the transmit transducer.

The pre-treatment value of the power may be less than the treatment value of the power.

The first one or more of the corresponding plurality of transmission parameters may comprise a pulse length of the ultrasound transmission by the transmit transducer.

The pre-treatment value of the pulse length may be less than the treatment value of the pulse length.

The method may also comprise injecting microbubbles into the patient before transmitting pre-treatment ultrasound energy into the brain of the patient. The method may also comprise injecting microbubbles into the patient during at least a portion of transmitting pre-treatment ultrasound energy into the brain of the patient.

The method may also comprise filtering the return pre-treatment signals to extract filtered return signals. Each filtered return signal may correspond to one of the plurality of receive transducers. Determining the treatment characteristic based at least in part on the received return pre-treatment signals may comprise determining the treatment characteristic based at least in part on the filtered return signals.

The second one or more of the corresponding plurality of transmission parameters may comprise a treatment frequency of the ultrasound transmission by the transmit transducer.

Filtering the return pre-treatment signals to extract filtered return signals may comprise band-pass filtering the return pre-treatment signals to extract, as the filtered return signals, one of: a fundamental (first harmonic) of the treatment frequency; and a higher order (e.g. $2^{nd}$ or higher order) harmonic of the treatment frequency.

The method may also comprise at least one of: injecting microbubbles into the patient before transmitting pre-treatment ultrasound energy into the brain of the patient and injecting microbubbles into the patient during at least a portion of transmitting pre-treatment ultrasound energy into the brain of the patient. The method may also comprise filtering the return pre-treatment signals to extract filtered return signals. Each filtered return signal may correspond to one of the plurality of receive transducers. Determining the treatment characteristic based at least in part on the received return pre-treatment signals may comprise determining the treatment characteristic based at least in part on the filtered return signals. The second one or more of the corresponding plurality of transmission parameters may comprise a treatment frequency of the ultrasound transmission by the transmit transducer. Filtering the return pre-treatment signals to extract filtered return signals may comprise band-pass filtering the return pre-treatment signals to extract, as the filtered return signals, a higher order (e.g. $2^{nd}$ or higher order) harmonic of the treatment frequency.

The treatment characteristic may be a treatment focus location of the proposed ultrasound treatment. The method may comprise determining a plurality of receive focus profiles $\phi_{x,v_i}$. Each receive focus profile $\phi_{x,v_i}$ may correspond to a candidate treatment focus location x from among a plurality of X candidate locations. Each receive focus profile $\phi_{x,v_i}$ may also correspond to an assumed ultrasound propagation velocity profile $v_i$ from among a plurality of I of assumed ultrasound propagation velocity profiles. Each receive focus profile $\phi_{x,v_i}$ may comprise N elements $\phi_{x,v_i}{}^n$, where N corresponds to a number of the plurality of receive transducers and the element $\phi_{x,v_i}{}^n$ may comprise a phase offset or a time offset for an $n^{th}$ one of the plurality of receive transducers. Determining the plurality of receive focus profiles $\phi_{x,v_i}$ may comprise, for each of the plurality of receive focus profiles $\phi_{x,v_i}$, determining the phase offset or the time offset for each element $\phi_{x,v_i}{}^n$ based on the candidate treatment focus location x, a location of the $n^{th}$ receive transducer relative to the treatment focus location x and the assumed velocity profile $v_i$. Determining the treatment characteristic based at least in part on the received return pre-treatment signals may comprise determining the treatment focus location based at least in part on the received return pre-treatment signals and the receive focus profiles $\phi_{x,v_i}$.

Determining the treatment focus location based at least in part on the received return pre-treatment signals and the receive focus profiles $\phi_{x,v_i}$ may comprise filtering the received return pre-treatment signals to extract filtered return signals, each filtered return signal corresponding to one of the receive transducers. Determining the treatment focus location based at least in part on the received return pre-treatment signals and the receive focus profiles $\phi_{x,v_i}$ may also comprise determining the treatment focus location based at least in part on the filtered return signals and the receive focus profiles $\phi_{x,v_i}$.

The second one or more of the corresponding plurality of transmission parameters may comprise a treatment frequency of the ultrasound transmission by the transmit transducer. Filtering the received return pre-treatment signals to extract filtered return signals may comprise filtering the received return pre-treatment signals using band pass filters. The band-pass filters may be configured to extract, as the filtered return signals, one of: a fundamental (first harmonic) of the treatment frequency; and a higher order (e.g. $2^{nd}$ or higher order) harmonic of the treatment frequency.

Determining the plurality of receive focus profiles $\phi_{x,v_i}$ may comprise determining each of the plurality of receive focus profiles $\phi_{x,v_i}$ at a focus-profile frequency that corresponds to the one of: the fundamental (first harmonic) of the treatment frequency; and the higher order (e.g. $2^{nd}$ or higher order) harmonic of the treatment frequency.

The method may also comprise at least one of: injecting microbubbles into the patient before transmitting pre-treatment ultrasound energy into the brain of the patient; and during at least a portion of transmitting pre-treatment ultrasound energy into the brain of the patient. The band-pass filters may be configured to extract, as the filtered return signals, a higher order (e.g. $2^{nd}$ or higher order) harmonic of the treatment frequency.

Determining the plurality of receive focus profiles $\phi_{x,v_i}$ may comprise determining each of the plurality of receive focus profiles $\phi_{x,v_i}$ at a focus-profile frequency that corresponds to the higher order (e.g. $2^{nd}$ or higher order) harmonic of the treatment frequency.

Determining the treatment focus location based at least in part on the filtered return signals and the receive focus profiles $\phi_{x,v_i}$ may comprise for each receive focus profile $\phi_{x,v_i}$ applying the receive focus profile $\phi_{x,v_i}$ to the filtered return signals to determine phase-adjusted signals or time-adjusted signals and summing the phase-adjusted signals or time-adjusted signals to determine a sum signal S corresponding to the receive focus profile $\phi_{x,v_i}$. Determining the treatment focus location based at least in part on the filtered return signals and the receive focus profiles $\phi_{x,v_i}$ may also comprise determining the focus location based at least in part on the sum signals $S_{x,v_i}$ corresponding to the plurality of receive focus profiles $\phi_{x,v_i}$.

Applying the receive focus profile $\phi_{x,v_i}$ to the filtered return signals to determine phase-adjusted signals or time-adjusted signals may comprise, for each filtered return signal, adjusting a phase of the filtered return signal by the phase offset of a corresponding element $\phi_{x,v_i}{}^n$ of the receive focus profile $\phi_{x,v_i}$ to thereby determine a corresponding phase-adjusted signal or adjusting a time of the filtered return signal by the time offset of a corresponding element $\phi_{x,v_i}^n$ of the receive focus profile $\phi_{x,v_i}$ to thereby determine a corresponding time-adjusted signal.

Determining the treatment focus location based at least in part on the sum signals $S_{x,v_i}$ corresponding to the plurality of receive focus profiles $\phi_{x,v_i}$ may comprise extracting a value $S_{x,v_i}^1$ from each sum signal $S_{x,v_i}$ and determining the treatment focus location based on the extracted values $S_{x,v_i}^1$.

Extracting a value $S_{x,v_i}^1$ from each sum signal $S_{x,v_i}$ may comprise at least one of integrating the sum signal $S_{x,v_i}$ corresponding to the receive focus profile $\phi_{x,v_i}$ to obtain the extracted value $S_{x,v_i}^1$ corresponding to the receive focus profile $\phi_{x,v_i}$ and extracting a maximum magnitude value from the sum signal $S_{x,v_i}$ corresponding to the receive focus profile $\phi_{x,v_i}$ to obtain the extracted value $S_{x,v_i}^1$ corresponding to the receive focus profile $\phi_{x,v_i}$.

Determining the treatment focus location based on the extracted values $S_{x,v_i}^1$ may comprise determining the treatment focus location to be the candidate treatment focus location x corresponding to the receive focus profile $\phi_{x,v_i}$ having the largest extracted value $S_{x,v_i}^1$ from among the extracted values corresponding to the plurality of receive focus profiles $\phi_{x,v_i}$.

Determining the treatment focus location based at least in part on the filtered return signals and the receive focus profiles $\phi_{x,v_i}$ may comprise cross-correlating each of the filtered return signals with a reference one of the filtered return signals or another one (e.g. a nearest neighbor of the plurality of receive transducers) of the filtered return signals to obtain a return phase offset or time offset profile $\gamma$, where the return phase offset or time offset profile $\gamma$ may comprise one cross-correlation parameter $\gamma_n$ for each of the plurality of receive transducers, the cross-correlation parameter $\gamma_n$ indicative of a phase offset or time offset of the $n^{th}$ filtered return signal relative to the reference filtered return signal. Determining the treatment focus location based at least in part on the filtered return signals and the receive focus profiles $\phi_{x,v_i}$ may also comprise determining the treatment focus location based at least in part on the return phase offset or time offset profile $\gamma$ and the plurality of receive focus profiles $\phi_{x,v_i}$.

The reference one of the filtered return signals used to obtain the return phase offset or time offset profile $\gamma$ may correspond to the filtered return signal from a reference one of the plurality of receive transducers used for determining the receive focus profiles $\phi_{x,v_i}$.

Determining the treatment focus location based at least in part on the return phase offset or time offset profile $\gamma$ and the plurality of receive focus profiles $\phi_{x,v_i}$ may comprise for each receive focus profile $\phi_{x,v_i}$, comparing the return phase offset or time offset profile $\gamma$ to the focus profile $\phi_{x,v_i}$ to obtain a corresponding similarity metric as between the return phase offset or time offset profile $\gamma$ and the receive focus profile $\phi_{x,v_i}$ and determining the focus location based on the similarity metrics for the plurality of receive focus profiles $\phi_{x,v_i}$.

Determining the treatment focus location based on the similarity metrics for the plurality of receive focus profiles $\phi_{x,v_i}$ may comprise determining the treatment focus location to be at the candidate treatment focus location x of the receive focus profile $\phi_{x,v_i}$ that is most similar to the return phase offset or time offset profile $\gamma$.

Determining the phase offset or time offset for each element $\phi_{x,v_i}^n$ may be based on a physical and acoustic model of the head of the patient to be treated by the ultrasound therapy system.

Determining the phase offset or time offset for each element $\phi_{x,v_i}^n$ may be based on at least one of: an estimated location of the $n^{th}$ receive transducer; and an estimated position of a structure (e.g. a cap) which supports the receive transducers relative to the head of the patient.

Determining the phase offset or time offset for each element $\phi_{x,v_i}^n$ may be based on an aligned model which specifies a physical and acoustic model of the head of the patient to be treated by the ultrasound therapy system and alignment between the model and at least one of: an estimated position of the $n^{th}$ receive transducer; and an estimated position of a structure (e.g. a cap) which supports the receive transducers relative to the head of the patient.

Determining the phase offset or time offset for each element $\phi_{x,v_i}^n$ may comprise selecting one (n*) of the plurality of receive transducers to be a reference transducer. Determining the phase offset or time offset for each element $\phi_{x,v_i}^n$ may also comprise for each element $\phi_{x,v_i}^n$ corresponding to an $n^{th}$ one of the plurality of receive transducers determining a phase or time $\psi_{x,v_i}^n$ of an ultrasound wave that would be received at the $n^{th}$ one of the plurality of receive transducers with the velocity profile $v_i$ from the candidate treatment focus location x based on a simulation of ultrasound propagation between the candidate treatment focus location x and the $n^{th}$ one of the plurality of receive transducers based on the velocity profile $v_i$. Determining the phase offset or time offset for each element $\phi_{x,v_i}^n$ may also comprise for each element $\phi_{x,v_i}^n$ corresponding to an $n^{th}$ one of the plurality of receive transducers determining $\phi_{x,v_i}^n$ to be a phase offset or time offset between the determined phase or time $\psi_{x,v_i}^n$ for the $n^{th}$ one of the plurality of receive transducers and the determined phase or time $\psi_{x,v_i}^{n*}$ of the reference transducer according to $\phi_{x,v_i}^n = \psi_{x,v_i}^n - \psi_{x,v_i}^{n*}$).

The method may also comprise graphically displaying the determined treatment focus location in an image of the brain of the patient.

Graphically displaying the determined treatment focus location may comprise graphically displaying one or more of a region of interest in the brain of the patient, a desired treatment focus location of the proposed ultrasound treatment and a beam simulation of the ultrasound treatment based on the determined treatment focus location wherein the beam simulation is performed with, for each of the plurality of transmit transducers, at least a subset of the treatment values for the corresponding plurality of transmission parameters.

Graphically displaying the determined treatment focus location may comprise graphically displaying the beam simulation. The beam simulation may include one or more regions (e.g. 0 to −3 dB; −3 bB to −6 dB and/or the like) of ultrasound pressure (e.g. peak-negative pressure) relative to ultrasound pressure at the determined treatment focus location.

Graphically displaying the determined treatment focus location may comprise displaying the determined treatment focus location in a three-dimensional representation of the brain of the patient.

The method may comprise, if the determined treatment characteristic is confirmed to be within a threshold similarity metric of the treatment characteristic, delivering ultrasound according to the proposed ultrasound treatment to open a blood brain barrier of the patient.

The plurality of transmission parameters may comprise beam-forming parameters.

One aspect provides a method for delivering ultrasound therapy using an ultrasound therapy system. The ultrasound therapy system may comprise a plurality of transmit transducers for transmitting ultrasound energy into the brain of a patient and a plurality of receive transducers for receiving reflected ultrasound energy from the brain of the patient. The method may comprise determining a desired treatment characteristic for treatment ultrasound energy to be delivered to the brain of the patient from the transmit transducers. The method may also comprise confirming the treatment characteristic according to any of the methods described herein. The method may also comprise delivering the treatment ultrasound energy to the brain of the patient from the transmit transducers only if the confirmed treatment characteristic is within a threshold similarity metric of the desired treatment characteristic.

One aspect provides an ultrasound therapy system. The ultrasound therapy system may comprise a plurality of transmit transducers for transmitting ultrasound energy into the brain of a patient. The ultrasound therapy system may also comprise a plurality of receive transducers for receiving reflected ultrasound energy from the brain of the patient. The ultrasound may also comprise a controller. The controller may be configured to obtain a proposed ultrasound treatment parameterized by, for each of the plurality of transmit transducers, treatment values for a corresponding plurality of transmission parameters. The controller may be configured to cause the transmit transducers to transmit pre-treatment ultrasound energy into the brain of the patient. Transmitting the pre-treatment ultrasound energy may comprise causing each of the plurality of transmit transducers to transmit ultrasound energy according to pre-treatment values for the corresponding plurality of transmission parameters. The pre-treatment values for a first one or more of the corresponding plurality of transmission parameters may be different than the treatment values for the first one or more of the corresponding plurality of transmission parameters and the pre-treatment values for a second one or more of the corresponding plurality of transmission parameters may be the same as the treatment values for the second one or more of the corresponding plurality of transmission parameters. The controller may be configured to receive return pre-treatment signals received at the plurality of receive transducers. The controller may be configured to determine the treatment characteristic based at least in part on the received return pre-treatment signals.

The ultrasound therapy system may comprise any of the features described herein. The controller may be configured to perform any of the features described herein.

One aspect provides a method for confirming a treatment focus location of a proposed ultrasound treatment to be effected by an ultrasound therapy system. The ultrasound therapy system may comprise a plurality of transmit transducers for transmitting ultrasound energy into the brain of a patient and a plurality of receive transducers for receiving reflected ultrasound energy from the brain of the patient. The method may comprise determining a plurality of receive focus profiles $\phi_{x,v_i}$. Each receive focus profile $\phi_{x,v_i}$ may correspond to a candidate treatment focus location x from among a plurality of X candidate locations and may correspond to an assumed ultrasound propagation velocity profile $v_i$ from among a plurality of I of assumed ultrasound propagation velocity profiles. Each receive focus profile $\phi_{x,v_i}$ may comprise N elements $\phi_{x,v_i}^n$ where N corresponds to a number of the plurality of receive transducers and the element $\phi_{x,v_i}^n$ may comprise a phase offset or time offset for an $n^{th}$ one of the plurality of receive transducers. Determining the plurality of receive focus profiles $\phi_{x,v_i}$ may comprise, for each of the plurality of receive focus profiles $\phi_{x,v_i}$, determining the phase offset or time offset for each element $\phi_{x,v_i}^n$ based on the candidate treatment focus location x, a location of the $n^{th}$ receive transducer relative to the treatment focus location x and the assumed velocity profile $v_i$. The method may also comprise transmitting pre-treatment ultrasound energy into the brain of the patient using the plurality of transmit transducers. The method may also comprise receiving return pre-treatment signals at the plurality of receive transducers. Each return pre-treatment signal may correspond to one of the receive transducers. The method may also comprise determining the treatment focus location based at least in part on the received return pre-treatment signals and the receive focus profiles $\phi_{x,v_i}$.

Determining the treatment focus location based at least in part on the received return pre-treatment signals and the receive focus profiles $\phi_{x,v_i}$ may comprise filtering the received return pre-treatment signals to extract filtered return signals. Each filtered return signal may correspond to one of the receive transducers. Determining the treatment focus location based at least in part on the received return pre-treatment signals and the receive focus profiles $\phi_{x,v_i}$ may comprise determining the treatment focus location based at least in part on the filtered return signals and the receive focus profiles $\phi_{x,v_i}$.

Transmitting pre-treatment ultrasound energy into the brain of the patient may comprise transmitting ultrasound energy into the brain of the patient with a pre-treatment frequency that is the same as a treatment frequency proposed to be used by the ultrasound therapy system for the proposed ultrasound treatment. Filtering the received return pre-treatment signals to extract filtered return signals may comprise filtering the received return pre-treatment signals using band pass filters. The band-pass filters may be configured to extract, as the filtered return signals, one of: a fundamental (first harmonic) of the treatment frequency; and a higher order (e.g. $2^{nd}$ or higher order) harmonic of the treatment frequency.

Determining the plurality of receive focus profiles $\phi_{x,v_i}$ may comprise determining each of the plurality of receive focus profiles $\phi_{x,v_i}$ at a focus-profile frequency that corresponds to the one of: the fundamental (first harmonic) of the treatment frequency; and the higher order (e.g. $2^{nd}$ or higher order) harmonic of the treatment frequency.

The method may also comprise injecting microbubbles into the patient at least one of: before transmitting pre-treatment ultrasound energy into the brain of the patient; and during at least a portion of transmitting pre-treatment ultrasound energy into the brain of the patient. The band-pass filters may be configured to extract, as the filtered return signals, the higher order (e.g. $2^{nd}$ or higher order) harmonic of the treatment frequency.

Determining the plurality of receive focus profiles $\phi_{x,v_i}$ may comprise determining each of the plurality of receive focus profiles $\phi_{x,v_i}$ at a focus-profile frequency that corresponds to the higher order (e.g. $2^{nd}$ or higher order) harmonic of the treatment frequency.

Determining the treatment focus location based at least in part on the filtered return signals and the receive focus profiles $\phi_{x,v_i}$ may comprise for each receive focus profile $\phi_{x,v_i}$: applying the receive focus profile $\phi_{x,v_i}$ to the filtered return signals to determine phase-adjusted signals or time-adjusted signals; and summing the phase-adjusted signals or time-adjusted signals to determine a sum signal S corresponding to the receive focus profile $\phi_{x,v_i}$. Determining the treatment focus location based at least in part on the filtered return signals and the receive focus profiles $\phi_{x,v_i}$ may comprise determining the treatment focus location based at least in part on the sum signals $S_{x,v_i}$ corresponding to the plurality of receive focus profiles $\phi_{x,v_i}$.

Applying the receive focus profile $\phi_{x,v_i}$ to the filtered return signals to determine phase-adjusted signals or time-adjusted signals may comprise, for each filtered return signal, adjusting a phase of the filtered return signal by the phase offset of a corresponding element $\phi_{x,v_i}^n$ of the receive focus profile $\phi_{x,v_i}$ to thereby determine a corresponding phase-adjusted signal or adjusting a time of the filtered return signal by the time offset of a corresponding element $\phi_{x,v_i}^n$ of the receive focus profile $\phi_{x,v_i}$ to thereby determine a corresponding time-adjusted signal.

Determining the treatment focus location based at least in part on the sum signals $S_{x,v_i}$ corresponding to the plurality of receive focus profiles $\phi_{x,v_i}$ may comprise: extracting a value $S_{x,v_i}^1$ from each sum signal $S_{x,v_i}$; and determining the treatment focus location on the extracted values $S_{x,v_i}^1$.

Extracting a value $S_{x,v_i}^1$ from each sum signal $S_{x,v_i}$ may comprise at least one of: integrating the sum signal $S_{x,v_i}$ corresponding to the receive focus profile $\phi_{x,v_i}$ to obtain an integrated extracted value $S_{x,v_i}^1$ corresponding to the receive focus profile $\phi_{x,v_i}$; and extracting a maximum magnitude value from the sum signal $S_{x,v_i}$ corresponding to the receive focus profile $\phi_{x,v_i}$ to obtain the extracted value $S_{x,v_i}^1$ corresponding to the receive focus profile $\phi_{x,v_i}$.

Determining the treatment focus location based on the extracted values $S_{x,v_i}^1$ may comprise determining the treatment focus location to be the candidate treatment focus location x corresponding to the receive focus profile $\phi_{x,v_i}$ having the largest extracted value $S_{x,v_i}^1$ from among the extracted values corresponding to the plurality of receive focus profiles $\phi_{x,v_i}$.

Determining the treatment focus location based at least in part on the filtered return signals and the receive focus profiles $\phi_{x,v_i}$ may comprise cross-correlating each of the filtered return signals with a reference one of the filtered return signals or another one (e.g. a nearest neighbor of the plurality of receive transducers) of the filtered return signals to obtain a return phase offset or time offset profile γ. The return phase offset or time offset profile γ may comprise one cross-correlation parameter $γ_n$ for each of the plurality of receive transducers. The cross-correlation parameter $γ_n$ may be indicative of a phase offset or time offset of the $n^{th}$ filtered return signal relative to the reference filtered return signal. Determining the treatment focus location based at least in part on the filtered return signals and the receive focus profiles $\phi_{x,v_i}$ may comprise determining the treatment focus location based at least in part on the return phase offset or time offset profile γ and the plurality of receive focus profiles $\phi_{x,v_i}$.

The reference one of the filtered return signals used to obtain the return phase offset or time offset profile γ may correspond to the filtered return signal from a reference one of the plurality of receive transducers used for determining the receive focus profiles $\phi_{x,v_i}$.

Determining the treatment focus location based at least in part on the return phase offset or time offset profile γ and the plurality of receive focus profiles $\phi_{x,v_i}$ may comprise: for each receive focus profile $\phi_{x,v_i}$, comparing the return phase offset or time offset profile γ to the receive focus profile $\phi_{x,v_i}$ to obtain a corresponding similarity metric as between the return phase offset or time offset profile γ and the receive focus profile $\phi_{x,v_i}$; and determining the focus location based on the similarity metrics for the plurality of receive focus profiles $\phi_{x,v_i}$.

Determining the treatment focus location based on the similarity metrics for the plurality of receive focus profiles $\phi_{x,v_i}$ may comprise determining the treatment focus location to be at the candidate treatment focus location x of the receive focus profile $\phi_{x,v_i}$ that is most similar to the return phase offset or time offset profile γ.

Determining the phase offset or time offset for each element $\phi_{x,v_i}^n$ may be based on a physical and acoustic model of a head of the patient to be treated by the ultrasound therapy system.

Determining the phase offset or time offset for each element $\phi_{x,v_i}^n$ may be based on at least one of: an estimated position of the $n^{th}$ receive transducer; and an estimated position of a structure (e.g. a cap) which supports the receive transducers relative to the head of the patient.

Determining the phase offset or time offset for each element $\phi_{x,v_i}^n$ may be based on an aligned model which specifies a physical and acoustic model of a head of the patient to be treated by the ultrasound therapy system and alignment between the model and at least one of: an estimated position of the $n^{th}$ receive transducer; and an estimated position of a structure (e.g. a cap) which supports the receive transducers relative to the head of the patient.

Determining the phase offset or time offset for each element $\phi_{x,v_i}^n$ may comprise selecting one (n*) of the plurality of receive transducers to be a reference transducer. Determining the phase offset or time offset for each element $\phi_{x,v_i}^n$ may comprise for each element $\phi_{x,v_i}^n$ corresponding to an $n^{th}$ one of the plurality of receive transducers determining a phase or time $\psi_{x,v_i}^n$ of an ultrasound wave that would be received at the $n^{th}$ one of the plurality of receive transducers with the velocity profile $v_i$ from the candidate treatment focus location x based on a simulation of ultrasound propagation between the candidate treatment focus location x and the $n^{th}$ one of the plurality of receive transducers based on the velocity profile $v_i$. Determining the phase offset or time offset for each element $\phi_{x,v_i}^n$ may comprise for each element $\phi_{x,v_i}^n$ corresponding to an $n^{th}$ one of the plurality of receive transducers determining $\phi_{x,v_i}^n$ to be a phase offset or time offset between the determined phase or time $\psi_{x,v_i}^n$ for the $n^{th}$ one of the plurality of receive transducers and the determined phase or time $\psi_{x,v_i}^n$ of the reference transducer according to $\phi_{x,v_i}^n = \psi_{x,v_i}^n - \phi_{x,v_i}^{n*}$).

The method may also comprise injecting microbubbles into the patient at least one of: before transmitting pre-treatment ultrasound energy into the brain of the patient; and during at least a portion of transmitting pre-treatment ultrasound energy into the brain of the patient.

The proposed ultrasound treatment may be parameterized by, for each of the plurality of transmit transducers, treatment values for a corresponding plurality of transmission parameters. Transmitting pre-treatment ultrasound energy into the brain of the patient using the plurality of transmit transducers may comprise causing each of the plurality of transmit transducers to transmit ultrasound energy according to pre-treatment values for the corresponding plurality of transmission parameters. The pre-treatment values for a first one or more of the corresponding plurality of transmission parameters may be different than the treatment values for the first one or more of the corresponding plurality of transmission parameters and the pre-treatment values for a second one or more of the corresponding plurality of transmission parameters may be the same as the treatment values for the second one or more of the corresponding plurality of transmission parameters.

The first one or more of the corresponding plurality of transmission parameters may be one of the corresponding plurality of transmission parameters.

The first one or more of the corresponding plurality of transmission parameters may comprise a power of the ultrasound transmission by the transmit transducer.

The pre-treatment value of the power may be less than the treatment value of the power.

The first one or more of the corresponding plurality of transmission parameters may comprise a pulse length of the ultrasound transmission by the transmit transducer.

The pre-treatment value of the pulse length may be less than the treatment value of the pulse length.

The second one or more of the corresponding plurality of transmission parameters may comprise a frequency of the ultrasound transmission by the transmit transducer.

The method may also comprise graphically displaying the determined treatment focus location in an image of the brain of the patient.

Graphically displaying the determined treatment focus location may comprise graphically displaying one or more of a region of interest in the brain of the patient, a desired treatment focus location of the proposed ultrasound treatment, and a beam simulation of the ultrasound treatment based on the determined treatment focus location wherein the beam simulation is performed with, for each of the plurality of transmit transducers, at least a subset of the treatment values for the corresponding plurality of transmission parameters.

Graphically displaying the determined treatment focus location may comprise graphically displaying the beam simulation. The beam simulation may include one or more regions (e.g. 0 to −3 dB; −3 bB to −6 dB and/or the like) of ultrasound pressure (e.g. peak-negative pressure) relative to ultrasound pressure at the determined treatment focus location.

Graphically displaying the determined treatment focus location may comprise displaying the determined treatment focus location in a three-dimensional representation of the brain of the patient.

The method may comprise, if the determined treatment characteristic is confirmed to be within a threshold similarity metric of the treatment characteristic, delivering ultrasound according to the proposed ultrasound treatment to open a blood brain barrier of the patient.

The plurality of transmission parameters may comprise beam-forming parameters.

One aspect provides a method for delivering ultrasound therapy using an ultrasound therapy system. The ultrasound therapy system may comprise a plurality of transmit transducers for transmitting ultrasound energy into the brain of a patient and a plurality of receive transducers for receiving reflected ultrasound energy from the brain of the patient. The method may comprise determining a desired treatment focus location for treatment ultrasound energy to be delivered to the brain of the patient from the transmit transducers. The method may also comprise confirming a treatment focus location according to any of the methods described herein. The method may also comprise delivering the treatment ultrasound energy to the brain of the patient from the transmit transducers only if the confirmed treatment focus location is within a threshold distance of the desired treatment focus location.

One aspect provides an ultrasound therapy system. The ultrasound therapy system may comprise a plurality of transmit transducers for transmitting ultrasound energy into the brain of a patient. The ultrasound therapy system may also comprise a plurality of receive transducers for receiving reflected ultrasound energy from the brain of the patient. The ultrasound therapy system may also comprise a controller. The controller may be configured to determine a plurality of receive focus profiles $\phi_{x,v_i}$. Each receive focus profile $\phi_{x,v_i}$ may correspond to a candidate treatment focus location x from among a plurality of X candidate locations and may correspond to an assumed ultrasound propagation velocity profile $v_i$ from among a plurality of I of assumed ultrasound propagation velocity profiles. Each receive focus profile $\phi_{x,v_i}$ may comprise N elements $\phi_{x,v_i}^n$, where N corresponds to a number of the plurality of receive transducers and the element $\phi_{x,v_i}^n$ may comprise a phase offset or time offset for an $n^{th}$ one of the plurality of receive transducers. Determining the plurality of receive focus profiles $\phi_{x,v_i}$ may comprise, for each of the plurality of receive focus profiles $\phi_{x,v_i}$, determining the phase offset or time offset for each element $\phi_{x,v_i}^n$ based on the candidate treatment focus location x and the assumed velocity profile $v_i$. The controller may also be configured to cause the transmit transducers to transmit pre-treatment ultrasound energy into the brain of the patient. The controller may also be configured to receive return pre-treatment signals received at the plurality of receive transducers. Each return pre-treatment signal may correspond to one of the receive transducers. The controller may also be configured to determine the treatment focus location based at least in part on the received return pre-treatment signals and the receive focus profiles $\phi_{x,v_i}$.

The ultrasound system may also comprise any features described herein. The controller may be configured to perform any of the features described herein.

Further aspects and example embodiments are illustrated in the accompanying drawings and/or described in the following description.

It is emphasized that the invention relates to all combinations of the above features, even if these are recited in different claims.

BRIEF DESCRIPTION OF THE DRAWINGS

The accompanying drawings illustrate non-limiting example embodiments of the invention.

DETAILED DESCRIPTION

Figure 1:
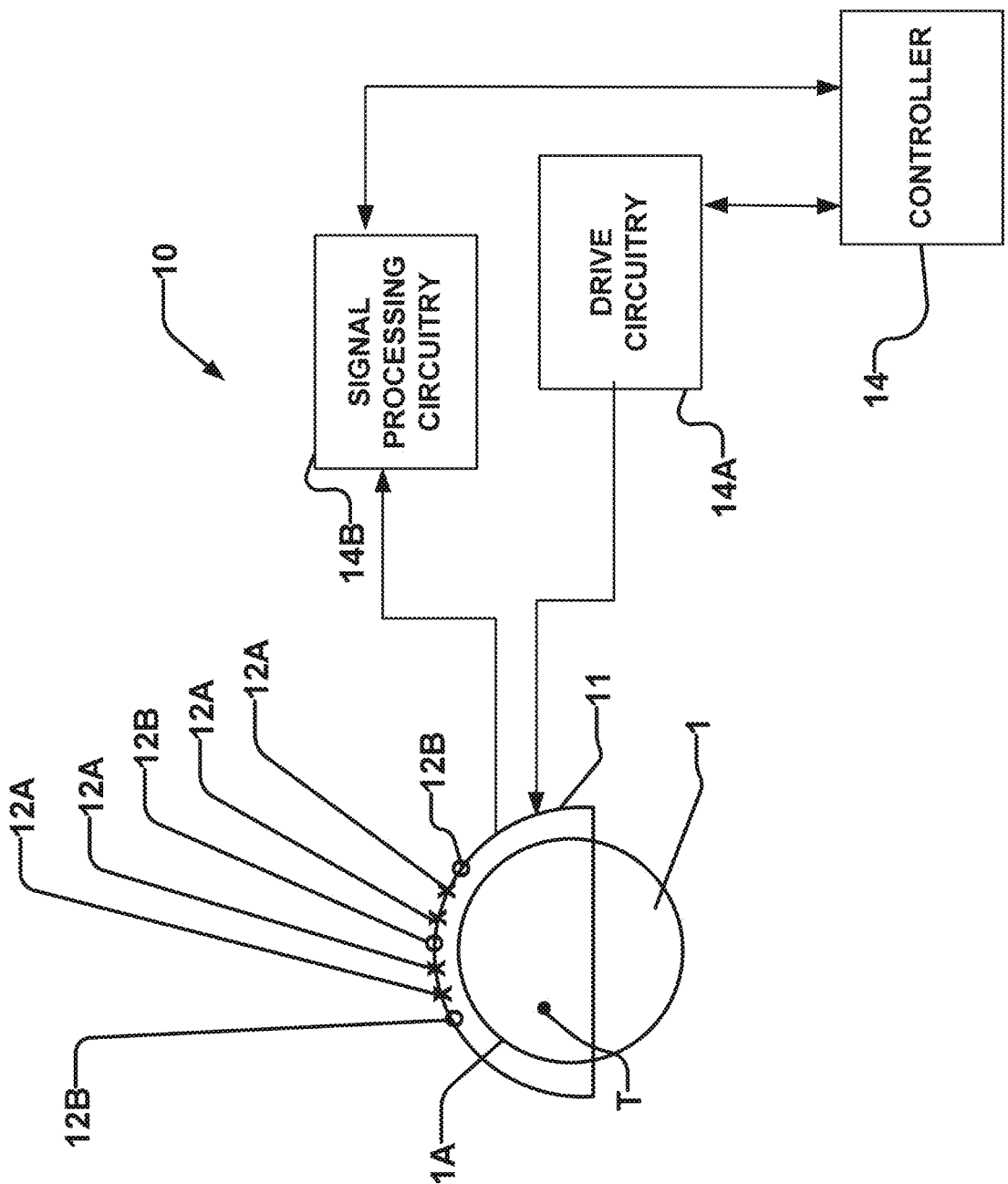
FIG. 1 is a schematic depiction of an ultrasound therapy system according to a particular example embodiment.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One aspect of this invention provides methods and systems for confirming the focus location of ultrasound energy to be delivered to a patient from a plurality of treatment ultrasound transducers as part of ultrasound therapy. The ultrasound energy delivered to a patient from the plurality of treatment ultrasound transducers as part of ultrasound therapy may be referred to herein as treatment ultrasound energy or, for brevity, treatment ultrasound. The location of focus of treatment ultrasound may be confirmed prior to the start of ultrasound therapy (in particular prior to delivery of treatment ultrasound energy to the subject). In some embodiments, ultrasound therapy may comprise delivering treatment ultrasound energy from the treatment ultrasound transducers through the skull to the brain of a patient. In some such applications, the delivery of treatment ultrasound energy to particular regions of the patient's brain results in peak negative pressure (i.e. a maximum amplitude negative pressure) having an amplitude that is greater than a threshold, which, in the presence of microbubbles, may in turn open a portion of the blood brain barrier of the patient. The blood brain barrier may be opened wherever the magnitude of the peak negative pressure is greater than the threshold. The magnitude of the peak negative pressure caused by the treatment ultrasound energy is typically greatest in a location corresponding to the focus of the treatment ultrasound energy (the treatment focus location). The blood brain barrier may also be opened in region(s) surrounding the treatment focus location if the magnitude of the peak negative pressure is sufficiently high (e.g. the blood brain barrier may be opened wherever the magnitude of the peak negative pressure is greater than a threshold).

Methods for confirming the treatment ultrasound focus location according to particular embodiments comprise: preparing the patient and ultrasound therapy system; determining a number of example receive focus profiles $\phi_{x,v_i}$ for particular candidate three-dimensional (3D) treatment focus locations and particular assumed ultrasound propagation velocity profiles (e.g. each receive focus profile $\phi_{x,v_i}$ for a particular candidate 3D treatment focus location x and a particular assumed velocity profile $v_i$ and each element $\phi_{x,v_i}^n$ of each receive focus profile $\phi_{x,v_i}$ comprising a phase offset or time offset for an $n^{th}$ one of a plurality of N receive transducers); optionally injecting microbubbles into the patient; performing a pre-treatment (e.g. low-power) ultrasound transmission into the brain of the patient using a plurality of transmission transducers; receiving return signals at the plurality of receive transducers; and determining the location of treatment focus based at least in part on the received return signals and the receive focus profiles $\phi_{x,v_i}$. Focus profiles $\phi_{x,v_i}$ may be determined for a particular focus-profile frequency. In some embodiments, multiple sets of focus profiles $\phi_{x,v_i}$ may be determined, with each set of focus profiles $\phi_{x,v_i}$ being determined for a corresponding particular focus-profile frequency. The focus-profile frequency may be the fundamental (first order harmonic) frequency or a higher order harmonic of a desired treatment frequency for treatment ultrasound energy. Determining the location of treatment focus based at least in part on the received return signals and the receive focus profiles $\phi_{x,v_i}$ may comprise filtering the received return signals to extract filtered return signals which may comprise a harmonic of the desired treatment frequency. Such filtered return signals may comprise the fundamental (first order harmonic) frequency or, in currently preferred embodiments, a higher order harmonic (e.g. $2^{nd}$ order harmonic, $3^{rd}$ order harmonic or the like). Determining the location of treatment focus based at least in part on the received return signals and the receive focus profiles $\phi_{x,v_i}$ may also comprise determining the location of treatment focus based at least in part on the filtered return signals and the receive focus profiles $\phi_{x,v_i}$. The selection of the focus-profile frequency may be based on the manner in which the received return signals are filtered. For example, if the received return signals are filtered with a band-pass filter corresponding to the fundamental frequency of the desired treatment frequency, then the focus-profile frequency may be selected to be the fundamental frequency of the desired treatment frequency. Similarly, if the received return signals are filtered with a band-pass filter corresponding to a higher-order (e.g. $2^{nd}$) harmonic of the desired treatment frequency, then the focus-profile frequency may be selected to be the higher-order (e.g. $2^{nd}$) harmonic of the desired treatment frequency.

In some embodiments, determining the location of treatment focus based at least in part on the filtered return signals and the receive focus profiles $\phi_{x,v_i}$ may comprise: applying each of the receive focus profiles $\phi_{x,v_i}$ to the filtered return signals to obtain phase-adjusted signals or time-adjusted signals; summing (and optionally integrating) the phase-adjusted signals or time-adjusted signals for each of the receive focus profiles $\phi_{x,v_i}$ to obtain a sum signal $S_{x,v_i}$ corresponding to each receive focus profile $\phi_{x,v_i}$; and confirming the location of treatment focus based at least in part on the sum signals $S_{x,v_i}$. Confirming the location of treatment focus based at least in part on the sum signals S may comprise extracting a value S from each sum $S_{x,v_i}$ and confirming the location of treatment focus based on comparing the extracted values $S_{x,v_i}^l$ for various receive focus profiles $\phi_{x,v_i}$. In some embodiments, extracting a value $S_{x,v_i}^l$ from each sum S may comprise integrating the magnitude of the sum $S_{x,v_i}$ over some suitable time (e.g. integration) window for the current receive focus profile $\phi_{x,v_i}$ to obtain the corresponding extracted value $S_{x,v_i}^l$. Confirming the location of treatment focus based on comparing the extracted values $S_{x,v_i}^l$ for various receive focus profiles $\phi_{x,v_i}$ may comprise confirming the location of treatment focus to be at the candidate treatment focus location x of the receive focus profile $\phi_{x,v_i}$ having the highest extracted value $S_{x,v_i}^l$.

In some embodiments, determining the location of treatment focus based at least in part on the filtered return signals and the receive focus profiles $\phi_{x,v_i}$ may comprise: cross-correlating each of the filtered return signals with a reference one of the filtered return signals to obtain a return phase offset or return time offset profile $\gamma$, where the return phase offset or return time offset profile $\gamma$ comprises one cross-correlation parameter $\gamma_n$ for each of the plurality of receive transducers, the cross-correlation parameter $\gamma_n$ indicative of a phase offset or time offset of the $n^{th}$ filtered return signal relative to the reference filtered return signal; and comparing the return phase offset or return time offset profile $\gamma$ to each of the receive focus profiles $\phi_{x,v_i}$ to determine a similarity metric as between the return phase offset or return time offset profile $\gamma$ and each of the receive focus profiles $\phi_{x,v_i}$. The receive transducer that is chosen to provide the reference filtered return signal used to determine the return phase offset or return time offset profile $\gamma$ may correspond to the same receive transducer used to determine the receive focus profiles $\phi_{x,v_i}$. Determining the location of treatment focus based at least in part on the filtered return signals and the receive focus profiles $\phi_{x,v_i}$ may comprise confirming the location of treatment focus based on comparing the similarity metrics for various receive focus profiles $\phi_{x,v_i}$. Confirming the location of treatment focus based on comparing the similarity metrics for various receive focus profiles $\phi_{x,v_i}$ may comprise confirming the location of treatment focus to be at the candidate treatment focus location x of the receive focus profile $\phi_{x,v_i}$ that is most similar to the return phase offset profile $\gamma$. Any suitable technique may be used to determine the similarity metric as between a return phase offset or return time offset profile γ and a corresponding receive focus profile $\phi_{x,v_i}$.

FIG. 1 shows a schematic depiction of an example ultrasound therapy system 10 according to a particular embodiment. Ultrasound therapy system 10 may be used to deliver ultrasound therapy (treatment ultrasound energy) to patient (or subject) 1. Ultrasound therapy system 10 may comprise cap (or similar structure) 11 that supports transducers 12 relative to head 1A of patient 1. Cap 11 may be positioned in any suitable manner on patient 1. For example cap 11 may be worn on the head 1A of patient 1 in a manner that is the same or similar to how a hat, helmet and/or beanie are worn. A surface of cap 11 may at least partially be in contact with or otherwise in acoustic contact (e.g. through a suitable acoustic transmission medium) with, the head 1A of patient 1. Cap 11 may at least partially comprise an elastic material which may facilitate the contact between the head 1A of patient 1 and cap 11 and/or secure cap 11 to patient 1, although this is not necessary and other techniques may be used to secure cap 11 to, or otherwise locate cap 11 relative to, patient 1.

Ultrasound therapy system 10 may also comprise one or more transmitting transducers 12A and one or more receiving transducers 12B (collectively referred to herein as transducers 12). Transducers 12 may be positioned and supported within cap 11. The locations of transducers 12 within cap 11 may be known, such that if a position of cap 11 is known relative to the subject's head, the positions of transducers 12 is also known relative to the same subject's head. In some embodiments, transducers 12 may come into direct contact with the head 1A of patient 1 when cap 11 is worn, although this is not necessary. In some embodiments, cap 11 may comprise or support one or more layers of ultrasound-transmitting medium (e.g. water) between transducers 12 and the head 1A of patient 1. Transducers 12 may be positioned in any suitable portion of cap 11. Transducers 12 may be positioned to be within one or more specific portions of cap 11 or generally span the entirety of cap 11. Transducers 12 may be, but need not be, positioned such that there is approximately an equal distance between transducers 12. In some embodiments, there may be variable distances between transducers 12.

Controller 14 is configured (using suitable drive circuitry 14A) to control transmit transducers 12A to emit ultrasound beams with desired treatment transmission parameters. For example, controller 14 may cause drive circuitry 14A to set an amplitude, phase, frequency and/or other parameters of the ultrasound wave to be emitted by each transmit transducer 12A. Controller 14 may set these treatment transmission parameters in an effort to make the ultrasound waves emitted by transmit transducers 12A converge at (i.e. be focused at) an intended target treatment focus location T. Such transmission parameters may comprise some of or all of so-called beam-forming parameters, which comprise a set of parameters which are used by the plurality of ultrasound transducers 12A to output a treatment ultrasound beam or treatment ultrasound energy. Such transmission parameters may additionally comprise a transmission power. Drive circuitry 14A may comprise, without limitation, digital to analog converters, amplifiers and/or the like. Typically, controller 14 sets treatment values using drive circuitry 14A for the amplitude, phase, frequency and/or other parameters of the ultrasound waves to be emitted by each of transmit transducers 12A to cause the target T to be the intended treatment focus location. In some embodiments, transmit transducers 12A are divided into a plurality of sets (or arrays) of transducers 12A. Each set of transmit transducers 12A may be independently controlled (e.g. by controller 14 using drive circuitry 14A) to emit ultrasound waves intended to be focused at a different target T (or targets) than the other set(s) of transmit transducers 12A.

The signals detected by receive transducers 12B are processed by suitable analog and/or digital signal processing circuitry 14B, which may be controlled by controller 14. Signal processing circuitry 14B may comprise, without limitation, amplifiers analog to digital converters, digital signal processing (DSP) hardware and software, band-pass filters and/or the like. In some embodiments, receive transducers 12B are divided into a plurality of sets (or arrays) of transducers 12B. Signals from each set of receive transducers 12B may be independently processed (e.g. by controller 14 using signal processing circuitry 14B). Controller 14 (together with drive circuitry 14A and signal processing circuitry 14B) may be referred to herein as controller 14 without loss of generality. Controller 14 may perform some of the methods described herein.

Prior to confirming a treatment focus location and delivering treatment ultrasound as described herein, the positioning and/or orientation of one or more of transducers 12 in relation to cap 11, transducers 12 in relation to patient 1 and cap 11 in relation to patient 1 may be adjustable. Transducers 12 may be positioned/oriented in relation to patient 1 in positions/orientations that are suitable to deliver treatment ultrasound. The positioning/orientation of transducers 12 may vary between caps 11, between patients and/or for a single patient 1. The positioning/orientation of transducers 12 may be varied for a single patient 1 for example during different ultrasound therapy sessions and/or within a single ultrasound therapy session. Variation in the positioning/orientation of transducers 12 may allow for ultrasound therapy to be delivered more effectively. For example, variation in the positioning/orientation of transducers 12 may allow different regions of interest to be reached. Different regions of interest can additionally or alternatively be reached using beam steering.

Varying the position and/or orientation of cap 11 on the head 1A of patient 1 may vary the position of transducers 12 in relation to patient 1. In this sense, prior to confirming a treatment focus location and delivering treatment ultrasound as described herein, cap 11 may be positioned or oriented in any number of suitable positions/locations relative to the head 1A of patient 1.

Additionally and/or alternatively, prior to confirming a treatment focus location and delivering treatment ultrasound as described herein, the positions of transducers 12 in relation to cap 11 may be varied. For example, transducers 12 may be secured on, in, or to cap 11 in different positions for different uses. Transducers 12 may be secured on, in or to cap 11 using any suitable means or mounting or connection.

Figure 2:
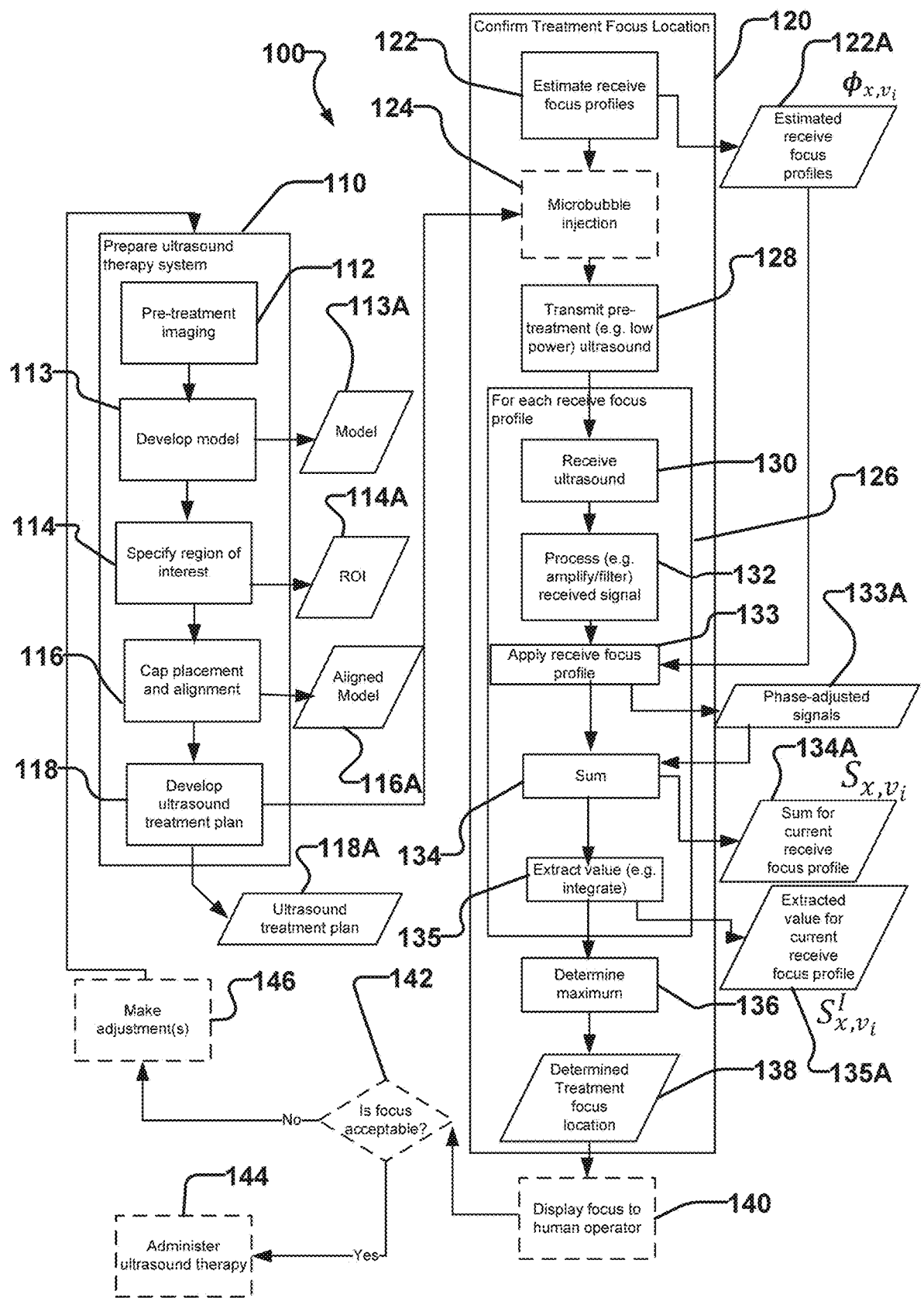
FIG. 2 is a flow chart of an example method for the confirmation of treatment focus location of ultrasound according to particular embodiment.

FIG. 2 is a flow chart of method 100 for confirming a treatment focus location of treatment ultrasound energy according to a particular embodiment. The treatment ultrasound energy may be applied to the head 1A of a patient 1 using an ultrasound therapy system 10 like that of FIG. 1, although this is not necessary and method 100 may be implemented using ultrasound therapy systems different from system 10. For ease of description and without limiting the generality of method 100 to application with other ultrasound therapy systems, method 100 is described herein with application to the FIG. 1 ultrasound therapy system 10.

Method 100 starts at block 110 which involves preparing ultrasound therapy system 10 for treatment. Block 110 starts at block 112 which involves pre-treatment imaging. Pre-treatment imaging in block 112 may comprise capturing images of patient 1. Such block 112 imaging may comprise any one or more of computed tomography (CT) imaging, magnetic resonance imaging (MRI), x-ray imaging, and/or the like. Block 110 then proceeds to block 113 which involves using the images obtained in block 112 to create a 3D model 113A of the imaged region of patient 1. Model 113A may comprise an acoustic and physical model 113A, where a physical model represents the dimensions (e.g. shape and/or thickness) of layers of object being modelled and an acoustic model assigns properties to each layer that affect the sound propagation in the layer (e.g. density, sound velocity and/or the like). For example, block 113 may involve creating a 3D acoustic and physical model 113A of the head 1A (including, for example, the skull and brain) of patient 1.

Block 110 then proceeds to block 114 which involves specifying one or more region(s) of interest 114A to be treated in the head 1A of patient 1. Such regions of interest 114A may be identified in model 113A or, in some embodiments, such regions of interest 114A may be identified as part of pre-treatment imaging in block 112 and transformed into an appropriate region of interest 114A in model 113A. Such regions of interest 114A may be identified by a physician or other medical practitioner. Such region(s) of interest 114A may comprise region(s) to which treatment ultrasound energy should be delivered and/or region(s) where the blood brain barrier should be opened by delivery of sufficient treatment ultrasound energy (e.g. with peak negative pressure greater than some configurable value). One or more treatment focal locations may be desired in these regions of interest 114A. In other forms of ultrasound treatments (e.g. ultrasound ablation, neuromodulation and/or the like), regions of interest 114A may be identified based on other suitable treatment objectives. Region(s) of interest 114A may generally have any shape or size.

Method 100 then proceeds to block 116 which involves placement of ultrasound therapy system 10 relative to head 1A of patient 1 for treatment of patient 1. In the case of ultrasound therapy system 10 in the FIG. 1 embodiment, block 116 may comprise putting cap 11 onto, and orienting cap 11 relative to, head 1A of patient 1. Block 116 may comprise determining an alignment (or registration) of cap 11 relative to the anatomy of the head 1A of patient 1 and, based on this alignment, block 116 may comprise determining positions of transducers 12 relative to the anatomy of head 1A of patient 1. Block 116 may also comprise determining an alignment of head 1A of patient 1 relative to model 113A. It will be appreciated that the alignment of cap 11 (or transducers 12) relative to head 1A of patient 1 and alignment of head 1A of patient 1 relative to model 113A provide alignment between model 113A and cap 11 (or transducers 12) on head 1A of patient 1. The model that results from the alignment between model 113A and cap 11 (or transducers 12) on head 1A of patient 1 may be referred to herein as the aligned model 116A. Particular and non-limiting examples of such alignment techniques are described in one or more of the PCT applications published under WO2018/026738 and WO2021/154730 which are hereby incorporated herein by reference. In some embodiments, block 116 may use any other suitable technique to determine the positions of transducers 12 relative to the anatomy of head 1A of patient 1 and/or head 1A of patient 1 relative to model 113A.

Block 110 then proceeds to block 118 which involves developing an ultrasound treatment plan 118A. Treatment plan 118A may be determined based on model 113, region of interest 114A and/or the locations of cap 11 and/or transducers 12. Treatment plan 118A may be determined by a suitably configured controller 14 (FIG. 1). Treatment plan 118A may involve specification of one or more desired treatment focus locations or targets T (at which treatment ultrasound energy should desirably be focused) for one or more corresponding successive and/or simultaneous ultrasound treatments to achieve desired clinical results in region of interest 114A. In some embodiments, for each ultrasound treatment that forms part of treatment plan 118A and for each corresponding desired treatment focal location (or target T), treatment plan 118A may comprise determining a subset of transducers 12 to be used for the corresponding treatment and a desired treatment frequency. Techniques for developing treatment plans 118A and desired treatment focus locations or targets T (at which treatment ultrasound energy should desirably be focused) in corresponding ultrasound treatments are described, for example, in the PCT applications published under WO2018/026738 and/or WO2021/154730. However the methods described herein are not limited to such techniques and any suitable technique can be used to determine one or more desired treatment focus locations or targets T (at which treatment ultrasound energy should desirably be focused). Any such ultrasound treatments may be applied successively or simultaneously as part of an ultrasound treatment plan.

Method 100 then proceeds to block 120 which involves confirming the treatment focus location of the ultrasound therapy system 10 prepared in block 110 on patient 1. The schematic illustration of FIG. 2 shows only one iteration of block 120. However, block 120 may be performed to confirm the treatment focal location for each successive or simultaneous treatment in treatment plan 118A and for each corresponding desired treatment focal location (or target T). In this sense, block 120 as described herein involves the confirmation of a single desired treatment focal location (or target T).

Block 120 begins in block 122, which involves determining a plurality of receive focus profiles $\phi_{x,v_i}$ (122A). Each receive focus profile $\phi_{x,v_i}$ (122A) may be determined for a particular candidate treatment focus location x within aligned 3D model 116A and for a particular assumed ultrasound propagation velocity profile $v_i$ in head 1A of patient 1. Receive focus profiles $\phi_{x,v_i}$ (122A) may be determined on the basis of aligned model 116A, which may be an aligned 3D model 116A (after model 113A is aligned or registered to cap 11 (or to transducers 12) in block 116). As described in more detail below, determining receive focus profiles $\phi_{x,v_i}$ (122A) may involve beam tracing from candidate treatment focus locations x to locations of transducers 12 in aligned (e.g. 3D) model 116A through a particular ultrasound propagation velocity profile $v_i$. The number X of candidate treatment focus locations x (x=1, 2 ... X) may comprise any suitable number of candidate treatment focus locations. Candidate treatment focus locations x may be evenly spaced apart in the volume of region of interest 114A or in any other volume of head 1 of patient 1A, I though such even spacing is not necessary. For example, candidate treatment focus locations x may be evenly spaced apart with example spacing intervals of half of the expected full-width-half-maximum of the focus of the ultrasound beam (in all three spatial dimensions) or any other suitable spacing which may be based, for example, on criteria such as available computational resources, desired processing time and/or desired clinical accuracy. Candidate treatment focus locations x may have a range that spans region of interest 114A and extends (by some suitable threshold number of candidates or by some suitable threshold distance) beyond region of interest 114A, for example. An example of a threshold distance (which candidate treatment focus locations x may extend beyond region of interest 114A may be an absolute distance (e.g. 1 cm, 2 cm and/or the like) or may be a relative distance (e.g. half of the smallest (in any of the three spatial dimensions) full-width-half-maximum of the ultrasound beam). The number I of assumed ultrasound velocity profiles $v_i$ ($v_1$, $v_2 \ldots v_I$) may be any suitable number of ultrasound velocity profiles. Each velocity profile $v_i$ is not limited to a single velocity and may comprise a number of velocities. For example, each velocity profile $v_i$ may be based on an assumed number of tissue layers or types (e.g. skull, brain tissue and/or the like) in model 113A. The range of assumed ultrasound propagation velocities within the set of velocity profiles $v_i$ may be based on published ranges of ultrasound propagation velocities in the heads (and/or in each layer of the heads) of patients. The resolution or discretization interval of assumed ultrasound velocity profiles $v_i$ may be selected based on criteria such as available computational resources, desired processing time and desired clinical accuracy.

Focus profiles $\phi_{x,v_i}$ (122A) may be determined in block 122 for a particular focus-profile frequency. The focus-profile frequency may be the fundamental (first harmonic) frequency or a higher order harmonic of the fundamental frequency of the desired treatment frequency for treatment ultrasound energy for a particular ultrasound treatment.

Each receive focus profile $\phi_{x,v_i}$ (122A) may comprise a vector of size N, where N is the number of receive transducers 12B in ultrasound therapy system 10. Each element $\phi_{x,v_i}^n$ (n=1, 2, 3 ... N) of each receive focus profile $\phi_{x,v_i}$ (122A) vector may correspond to a particular one (the $n^{th}$ one) of receive transducers 12B. Each element $\phi_{x,v_i}^n$ of each receive focus profile $\phi_{x,v_i}$ (122A) vector may specify a phase offset for the $n^{th}$ receive transducer 12B for the candidate treatment focus location x which may be determined based on the acoustic path from the candidate treatment focus location x to the $n^{th}$ receive transducer 12B for a particular assumed ultrasound velocity profile $v_i$. Each element $\phi_{x,v_i}^n$ of each receive focus profile $\phi_{x,v_i}$ (122A) may be determined using aligned (e.g. 3D) model 116A (or model 113A and transducer positions determined in block 116) by: (i) starting at a candidate treatment focus location x, determining an acoustic path length (using velocity profile $v_i$) to the $n^{th}$ receive transducer 12B; (ii) determining a phase $\psi_{x,v_i}^n$ of the ultrasound wave that would be received at the $n^{th}$ receive transducer 12B with the velocity profile $v_i$ from the candidate treatment focus location x based on the acoustic path length; and (iii) selecting one (n*) of the N receive transducers 12B to be a reference transducer and determining $\phi_{x,v_i}^n$ for the $n^{th}$ receive transducer 12B to be a phase offset between the determined phase $\psi_{x,v_i}^n$ for the $n^{th}$ receive transducer 12B and the determined phase $\psi_{x,v_i}^{n*}$ of the reference transducer (i.e. according to $\phi_{x,v_i}^n = \psi_{x,v_i}^n - \psi_{x,v_i}^{n*}$). Thus, when n=n*, it follows that $\phi_{x,v_i}^{n*}=0$. Typically, although not necessarily, n* is chosen to correspond to the transducer with the minimum phase delay value.

In some embodiments, time offsets may be used in addition to or in the alternative to phase offsets. As will be described further below, time offsets may be used in a manner similar to phase offsets. In embodiments, using time offsets, each element $\phi_{x,v_i}^n$ of each receive focus profile $\phi_{x,v_i}$ (122A) comprises a time offset. Each element $\phi_{x,v_i}^n$ of each receive focus profile $\phi_{x,v_i}$ (122A) may be determined using aligned (e.g. 3D) model 116A (or model 113A and transducer positions determined in block 116) by: (i) starting at a candidate treatment focus location x, determining an acoustic path length (using velocity profile $v_i$) to the $n^{th}$ receive transducer 12B; (ii) determining a time $\psi_{x,v_i}^n$ of the ultrasound wave that would be received at the $n^{th}$ receive transducer 12B with the velocity profile $v_i$ from the candidate treatment focus location x based on the acoustic path length; and (iii) selecting one (n*) of the N receive transducers 12B to be a reference transducer (with $\psi_{x,v_i}^{n*}=0$) and determining $\phi_{x,v_i}^n$ for the $n^{th}$ receive transducer 12B to be a time offset between the determined time $\psi_{x,v_i}^n$ for the $n^{th}$ receive transducer 12B and the determined time $\psi_{x,v_i}^{n*}$ of the reference transducer (i.e. according to $\phi_{x,v_i}^n = \psi_{x,v_i}^n - \psi_{x,v_i}^{n*}$). It will be appreciated from the foregoing that time offsets and phase offsets and related to one another and many be determined and used in an analogous manner. For brevity and without loss of generality, this disclosure describes the use of phase offsets, and unless the context expressly dictates otherwise, time offsets may be used in the place of phase offsets.

Determining receive focus profiles $\phi_{x,v_i}$ (122A) in block 122 may be based on transducer positions determined in block 116 (or on aligned model 116A which incorporates these transducer positions). As discussed above, transducer positions determined in block 116 may be determined using any suitable technique. In some embodiments, receive focus profiles $\phi_{x,v_i}$ (122A) may be determined in block 122 after the transducer positions are ascertained in block 116. In some embodiments, intermediate values for receive focus profiles $\phi_{x,v_i}$ (122A) may be pre-calculated based on some reference transducer positions (e.g. prior to determining actual transducer positions in block 116) and then such intermediate values may be updated (e.g. by suitable integration, interpolation and/or other processing) after determining actual transducer positions in block 116. Advantageously, the pre-calculation of intermediate values for receive focus profiles $\phi_{x,v_i}$ (122A) may be performed before cap 11 is applied to the head 1A of patient 1 (and before patient 1 is otherwise engaged with system 10). Further, updating such intermediate values after cap 11 is applied to the head 1A of patient 1 may be relatively fast (as compared to computing receive focus profiles $\phi_{x,v_i}$ (122A) from scratch (i.e. without using such intermediate values) after cap 11 is applied to the head 1A of patient 1), which may reduce treatment time (i.e. time which patient 1 is engaged with system 10). U.S. patent application No. 63/393,045 filed 28 Jul. 2022 (which is hereby incorporated herein by reference) describes a technique for rapid calculation of treatment transmission parameters for transmit transducers based on determining intermediate values prior to applying cap 11A to head 1A and the further processing the intermediate values to obtain treatment values once cap 11A is applied to head 1A and the positions of the transmit transducers is known. An analogous technique of pre-calculating intermediate values and then further processing the intermediate values once cap 11A is applied to head 1A and the positions of the receive transducers is known could be used to determine the elements $\phi_{x,v_i}^n$ of receive focus profiles $\phi_{x,v_i}$ (122A) in block 122.

Method 100 then proceeds to block 124 which involves the optional step of injecting microbubbles into the peripheral circulation of patient 1 (e.g. through an intravenous catheter). Injecting microbubbles in this manner causes the microbubbles to be distributed into the circulatory system of patient 1 including the circulatory system of the brain. The block 124 injection of microbubbles may be performed in accordance with any of the techniques described, for example, in the PCT publication No. WO2018/026738. The block 124 injection of microbubbles may comprise one or more discrete bolus injection(s) of microbubbles (e.g. sufficient to last for the remainder of method 100) and/or a continuous injection of microbubbles during method 100. As discussed in more detail below, the strength (e.g. amplitude and/or spectral power) of the second and other higher order harmonic signals reflected from head 1A of patient 1 increases dramatically (non-linearly) as a function of pressure experienced by the injected microbubbles. Consequently, reflected signals measured by receive transducers 12B (after application of receive focus profiles $\phi_{x,v_i}$ (122A)) corresponding to candidate treatment focus location x will be highest when candidate treatment focus location x is located at or close to the treatment focus location of the transmitted beam (where the magnitude of transmitted ultrasound pressure is greatest). The block 124 injection of microbubbles is not necessary and treatment focus location 138 can be determined without injection of microbubbles, but the block 124 injection of microbubbles makes the determination of treatment focus location 138 more apparent (as compared to other candidate treatment focus locations x).

Method 100 then proceeds to block 128 which involves transmitting pre-treatment ultrasound into the head 1A of patient 1 using some or all of transmit transducers 12A. In some embodiments, the pre-treatment ultrasound transmitted in block 128 is low-power ultrasound. For example, pre-treatment ultrasound transmitted in block 128 may have the same transmission parameters as specified by the current ultrasound treatment in ultrasound treatment plan 118A, except that the transmission power is below the power associated with therapeutic effect. In particular, the pre-treatment ultrasound transmitted in block 128 may have the same desired treatment frequency. For example, the pressure associated with the block 128 pre-treatment transmission may be below the threshold acoustic pressure at which the blood brain barrier will open or the block 128 pre-treatment transmission may be below the power at which ultrasound ablation or ultrasound neuromodulation may occur. For example, the block 128 transmission power may be less than a threshold which may be set as a fraction (e.g. 10% or 25% or 50%) of the desired treatment transmission power. Thus, for example, if the threshold peak negative pressure for opening the blood brain barrier at a treatment ultrasound frequency of 250 kHz is about 0.3 MPa (assuming microbubbles are present in the circulatory system of patient 1), then the low-power ultrasound (or the pre-treatment ultrasound) can be configured with a power such that the peak negative pressure less than 0.3 MPa (e.g. 0.15 MPa). In some embodiments, other than the transmission power, other characteristics of the block 128 pre-treatment transmission (e.g. pulse length, burst length, phase, frequency and/or the like) may be same as the characteristics of treatment ultrasound.

In some embodiments, parameters of the block 128 pre-treatment ultrasound transmission in addition to or in the alternative to power may be different from the parameters specified by the current ultrasound treatment in ultrasound treatment plan 118A. In this manner, as explained in more detail below, the block 128 pre-treatment ultrasound transmission provides the possibility to use the block 128 pre-treatment ultrasound transmission as a "test" transmission to confirm some aspect (e.g. treatment focus location) of the ultrasound treatment plan 118A and then to proceed with ultrasound treatment according to ultrasound treatment plan 118A to obtain a therapeutic effect. For example, in some embodiments described herein, the desired therapeutic effect is opening the blood brain barrier, which is dependent on ultrasound treatment power, and the block 128 pre-treatment ultrasound transmission can therefore be a low-power transmission. In some other embodiments, the therapeutic effect may be dependent on some other ultrasound transmission parameter, such as pulse length, in which case the block 128 pre-treatment ultrasound transmission can be a low-pulse-length transmission used to confirm some aspect (e.g. the treatment focus location) of a subsequently applied full-pulse-length treatment transmission.

In some embodiments, pre-treatment ultrasound transmission in block 128 may continue until reflected ultrasound energy is received in block 130 and all of the receive focus profiles #(122A) are applied and processed (e.g. in blocks 132, 133, 134). Additionally or alternatively, the block 128 pre-treatment ultrasound transmission need only continue until reflected ultrasound energy is received in block 130 and such received ultrasound energy may be digitized and saved to suitable memory for subsequent processing (e.g. the application of blocks 132, 133, 134).

Method 100 then enters loop 126 which comprises a number of steps which are performed once for each receive focus profile $\phi_{x,v_i}$ (122A). Loop 126 is schematically illustrated in FIG. 2 according to a particular logical flow. In some embodiments, some blocks or steps of loop 126 may occur simultaneously, may overlap temporally with one another or may occur in a different order than that shown in FIG. 2. Further, some elements shown as being part of loop 126 need only be performed once. For example, signals may be received in block 130, processed in block 132 and stored once and then may be subsequently processed for different receive focus profiles $\phi_{x,v_i}$—that is, blocks 130, 132 need not be part of loop 126. Loop 126 begins in block 130 which involves receiving return (e.g. reflected) ultrasound signals at each of N receive transducers 12B. Such block 130 received ultrasound signals may have originated from signals originally transmitted in transmit ultrasound block 128. For example, such block 130 received ultrasound signals may comprise echoes from the block 128 ultrasound transmissions. Received signals may be amplified and digitized. As mentioned above, in some embodiments, block 130 and optionally block 132 may be performed once (outside of loop 126) and such received ultrasound energy may be digitized and saved to suitable memory for subsequent processing (e.g. the application of blocks 133, 134), where such subsequent processing may be performed for each receive focus profile $\phi_{x,v_i}$ as part of loop 126.

As alluded to above, the block 124 injection of microbubbles into patient 1 causes the strength (e.g. amplitude and/or spectral power) of higher order harmonics (e.g. $2^{nd}$ order harmonics, $3^{rd}$ order harmonics or other higher order (non-fundamental) harmonics) of the signals reflected from head 1A of patient 1 to increase non-linearly as a function (e.g. square law) of pressure experienced by the injected microbubbles. As such, the block 124 injection of microbubbles may allow the block 130 received ultrasound signals to have higher order harmonic components that are strong in comparison to the higher order harmonics of the block 128 transmit signal (which may not have higher order harmonic components of significance or at all).

In block 132, the block 130 received signals from each of the N receive transducers 12B may be processed by suitable analog and/or digital signal processing circuitry/routines. In currently preferred embodiments, the block 130 received signals from each of the N receive transducers 12B is amplified and then filtered using a band pass filter centered around a particular higher order harmonic (e.g. a $2^{nd}$ order harmonic, a $3^{rd}$ order harmonic or some other higher order (non-fundamental) harmonic) of the block 128 transmit frequency (which, as discussed above, may be the same as the desired treatment frequency). In currently preferred embodiments, the block 130 received signals are amplified in the analog domain, converted into digital signals using suitable analog-to-digital converters and then band-pass filtered in the digital domain using a band-pass filter centered around the $2^{nd}$ harmonic, although conversion to the digital domain prior to band-pass filtering is not necessary, the received signals may alternatively be band-pass filtered in the analog domain and the fundamental frequency or other higher order harmonic may additionally or alternatively be extracted.

As discussed above, the selection of the focus-profile frequency for focus profiles $\phi_{x,v_i}$ (122A) determined in block 122 may be based on the manner in which the received return signals are filtered in block 132. For example, if the received return signals are filtered in block 132 with a band-pass filter corresponding to the fundamental (first harmonic) frequency of the desired treatment frequency or the block 128 pre-treatment frequency, then the focus-profile frequency for focus profiles $\phi_{x,v_i}$ (122A) determined in block 122 may be selected to be the fundamental frequency of the desired treatment frequency or the block 128 pre-treatment frequency. Similarly, if the received return signals are filtered in block 132 with a band-pass filter corresponding to a higher-order (e.g. $2^{nd}$) harmonic of the desired treatment frequency or the block 128 pre-treatment frequency, then the focus-profile frequency for focus profiles $\phi_{x,v_i}$ (122A) determined in block 122 may be selected to be the higher-order (e.g. $2^{nd}$) harmonic of the desired treatment frequency or the block 128 pre-treatment frequency.

It will be appreciated by those skilled the art based on this disclosure that other suitable signal conditioning circuitry and/or functionality may be used in block 132 to process the block 130 received signals. It will also be apparent to those skilled in the art that blocks 130 and 132 may be performed once (e.g. outside of loop 126) and the signals output from block 132 may be digitized and stored for subsequent processing.

After processing (e.g. amplifying and filtering) the signals from each of the N receive transducers 12B in block 132, method 200 proceeds to block 133 which involves applying the current receive focus profile $\phi_{x,v_i}$ (122A) vector to the processed signals output from block 132 to determine phase-adjusted signals 133A corresponding to the current receive focus profile $\phi_{x,v_i}$ (122A). As discussed above, each element $\phi_{x,v_i}^n$ of each receive focus profile $\phi_{x,v_i}$ (122A) vector may comprise a phase offset for a corresponding one of the N receive transducers 12B. Application of the current receive focus profile $\phi_{x,v_i}$ (122A) vector to the processed signals output from block 132 may comprise applying (e.g. adding, subtracting or otherwise applying) these phase offsets to/from the phase of processed signals output from block 132 (e.g. to advance or retard the phases of the processed signals output from block 132) to determine corresponding phase-adjusted signals 133A. As also discussed above, each element $\phi_{x,v_i}^n$ of each receive focus profile $\phi_{x,v_i}$ (122A) vector may comprise a time offset for a corresponding one of the N receive transducers 12B. Application of the current receive focus profile $\phi_{x,v_i}$ (122A) vector to the processed signals output from block 132 may comprise applying (e.g. adding, subtracting or otherwise applying) these time offsets to/from the time of processed signals output from block 132 (e.g. to advance or retard the processed signals output from block 132 in the time domain). Accordingly, references herein to phase-adjusted signals 133A should be understood to include signals 133A adjusted by time offsets.

The inventors have determined that, within the phase adjusted signals 133A of successive iterations of loop 126, the magnitude of the harmonics of the block 128 transmit frequency (including the fundamental (first harmonic) frequency, but, in particular, the $2^{nd}$ order harmonic and/or other higher order harmonics) will be largest when the candidate treatment focus location x of the receive focus profile $\phi_{x,v_i}$ (using the velocity profile $v_i$ that is closest to the actual velocity profile in the head 1A of patient 1) corresponds to the actual treatment focus location of the block 128 transmission. Advantageously, where method 100 takes advantage of the optional block 124 injection of microbubbles, the differences between the phase-adjusted signals 133A and the sum signals $S_{x,v_i}$ (134A) (discussed further below) for different candidate treatment focus locations x and different velocity profiles $v_i$ corresponding to different receive focus profiles $\phi_{x,v_i}$ will be relatively pronounced (as compared without optional microbubble injection).

Method 100 then proceeds to block 134 which comprises summing the phase-adjusted signals 133A over the plurality of N receive transducers 12B to determine a sum signal $S_{x,v_i}$ (134A) for the current receive focus profile $\phi_{x,v_i}$. Summing the phase-adjusted signals 133A may be done in the radio frequency (RF) domain if analog circuitry is used or in the sample domain if digital circuitry is used. Method 100 then proceeds to block 135 which involves extracting a value $S_{x,v_i}^1$ (135A) from the block 134 sum signal $S_{x,v_i}$ (134A). In some embodiments, block 135 may comprise integrating the magnitude of the sum signal $S_{x,v_i}$ (134A) over some suitable time (e.g. integration) window for the current receive focus profile $\phi_{x,v_i}$ to extract a single value $S_{x,v_i}^1$ (135A) corresponding to the sum signal $S_{x,v_i}$ (134A). Such integration may pronounce differences between the sum signals $S_{x,v_i}$ (134A) for various receive focus profiles $\phi_{x,v_i}$. In other embodiments, other techniques could be used in block 135 to extract a value $S_{x,v_i}^1$ (135A) from the block 134 sum signals $S_{x,v_i}$ (134A). For example, in some embodiments, block 135 may comprise extracting a maximum magnitude value from sum signal $S_{x,v_i}$ (134A) to obtain extracted value $S_{x,v_i}^1$ (135A) or block 135 may comprise extracting some average magnitude value from sum signal $S_{x,v_i}$ (134A) to obtain extracted value $S_{x,v_i}^1$ (135A). In an example, for the blood-brain barrier opening application with focused ultrasound, the burst of ultrasound that is typically used is 10 ms with a burst rate of 1 Hz. Thus, in the low-power (pre-treatment) mode, these same parameters may be used (except for the transmit power being low). In such an example, the integration can happen over 10 ms or some fraction thereof such as 5 ms, for example. After one integration is complete or the single value $S_{x,v_i}^1$ is extracted, the process of loop 126 can commence for another receive focus profile $\phi_{x,v_i}$.

FIG. 2 depicts the functional components of method 100 in a particular order and groups together particular functional blocks for ease of explanation. This need not be the case in all embodiments. In some embodiments, unless the context dictates otherwise, the execution of various blocks of method 100 may occur simultaneously, may overlap in time with one or more other blocks of method 100 or may be executed in a different order. For example, at least a portion of receive ultrasound block 130 may overlap with a portion of transmit ultrasound block 128. For example, as soon as transmitting transducers 12A begin transmitting ultrasound as part of block 128, receiving transducers 12B may begin receiving reflected ultrasound signals as part of block 130. As another example, return signals may be received in block 130, processed in block 132 and stored once and then may be subsequently processed for different receive focus profiles $\phi_{x,v_i}$—that is, blocks 130, 132 need not be part of loop 126. As yet another example, where a treatment plan involves multiple targets, return signals for the plurality of targets may be simultaneously captured in block 130 (e.g. using different sets of receive transducers) and either simultaneously processed or serially processed through the other blocks.

It will be appreciated that at the conclusion of loop 126 for all of the receive focus profiles $\phi_{x,v_i}$ (122A), method 100 will have generated a plurality of extracted values $S_{x,v_i}^l$ (135A). The number of extracted values $S_{x,v_i}^l$ (135A) generated in loop 126 will be a product of the number X of candidate treatment focus locations x and the number I of assumed ultrasound velocity profiles $v_i$ for each candidate treatment focus location x.

After execution of loop 126, method 100 proceeds to block 136 which involves selecting a maximum one of the extracted values $S_{x,v_i}^l$ (135A) determined in loop 126 and determining that the treatment focus location 138 corresponds to the location x of the maximum one of the extracted values $S_{x,v_i}^l$ (135A). If there are two or more maximal extracted values $S_{x,v_i}^l$ (135A), then a suitable technique may be used to select a determined treatment focus location 138 based on the receive focus profiles $\phi_{x,v_i}$ (122A) corresponding to the two or more maximal extracted values $S_{x,v_i}^l$ (135A). By way of non-limiting example, such a technique may comprise: allowing a user to select the location x of one of the receive focus profiles $\phi_{x,v_i}$ (122A) corresponding the two or more maximal extracted values $S_{x,v_i}^l$ (135A); averaging the locations x of the receive focus profiles $\phi_{x,v_i}$ (122A) corresponding to the two or more maximal extracted values $S_{x,v_i}^l$ (135A); and/or the like. In some embodiments, where there are two or more maximal extracted values $S_{x,v_i}^l$ (135A), method 100 may output a message or other output indicating that the treatment focus confirmation was not successful, that treatment ultrasound energy should not be delivered to the patient because focus could not be confirmed and/or the like. In some embodiments, block 136 may comprise outputting the determined treatment focus location 138 (e.g. in a format that is suitable for interpretation by a human operator and/or by a suitable processor (e.g. a processor (not shown) associated with ultrasound therapy system 10). In some embodiments, the output of determined treatment focus location 138 (as part of block 136 or otherwise) may conclude method 100—i.e. method 100 may be complete with the output of determined focus location 138. As discussed above, the treatment focus confirmation of block 120 may be performed for each ultrasound treatment (and each corresponding treatment focus location) within treatment plan 118A. As such, method 100 may conclude after a number of iterations of treatment focus confirmation block 120 and a number of determined treatment focus locations 138.

The remaining steps of method 100 (described in more detail below) may be optional and may be performed in some embodiments. Although only shown once in the illustrated embodiment of FIG. 2, the remaining steps of method 100 may be performed for each determined treatment focus location 138.

Method 100 may optionally proceed to block 140 which involves displaying the determined treatment focus location 138 (e.g. in a format that is suitable for interpretation by a human operator). For example, block 140 may comprise generating a print or digital 2D image or 3D model of head 1A patient 1 (which may be based, for example, on the block 112 image(s) and/or 3D model) that relationally displays determined treatment focus location 138. For brevity, the 2D image and/or 3D model output in block 140 may be referred to herein as an image without loss of generality. The determined treatment location 138 displayed as part of the block 140 image may comprise some area (in the case of a 2D image) or some volume (in the case of a 3D image). Such area or volume may be determined on the basis of a discretization interval of candidate treatment locations x. The block 140 image may also relationally display the block 114 region of interest and/or the desired treatment focus location for a particular ultrasound treatment within treatment plan 118A. In some embodiments, the block 140 image may comprise a block 112 pre-treatment image (e.g. a CT image, a MRI image and/or a combination a CT/MRI image) with the determined treatment focus location 138, optionally the block 114 region of interest overlaid on top of the pre-treatment image and optionally the desired treatment focus location overlaid on top of the pre-treatment image. The block 140 display/image may comprise schematic depictions of some or all elements of ultrasound therapy system 10. The block 140 display/image may be manipulable (e.g. to zoom, pan, rotate and/or the like) by a human operator.

Figure 4A:
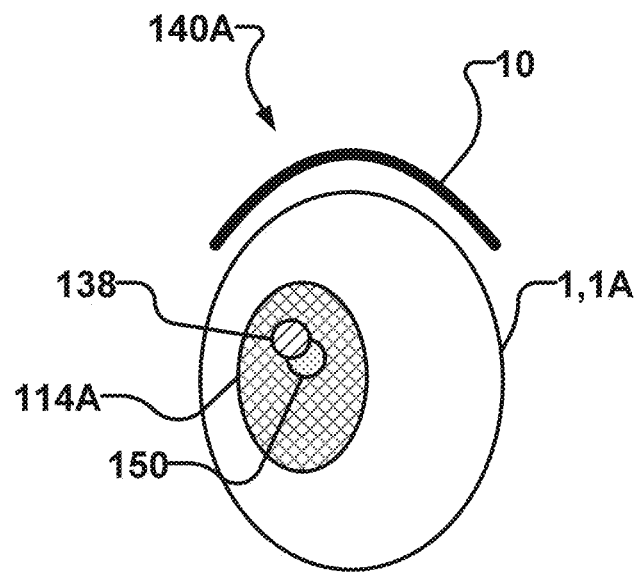
FIGS. 4A and 4B are example images of a determined treatment ultrasound focus location together with an image of the head of a patient that may be displayed in the FIG. 2 and/or FIG. 3 methods according to example embodiments.
Figure 4B:
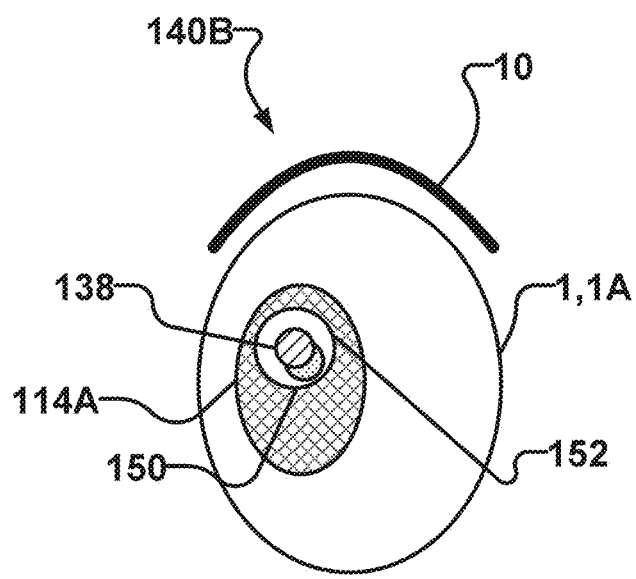

FIGS. 4A and 4B are example block 140 images 140A, 140B of a determined treatment focus location 138 together with an image of the head 1A of a patient 1 that may be displayed as part of optional block 140. In the FIG. 4A example, image 140A also includes an optional display of a region of interest 114A and a desired treatment focus location 150. In the FIG. 4B example, image 140B also includes an optional display of a beam simulation which may include, for example, a pressure region 152 that is outside of the determined treatment focus location 138 and/or the desired treatment focus location 150. For example, pressure region 152 may represent a 0 to −3 db pressure region (relative to simulated, estimated, ex vivo measured or otherwise determined pressure at determined treatment focus location 138). It will be appreciated that other pressure regions can be part of the option block 140 display. The beam simulations, calculations, estimations or other methods used to calculate the regions such as regions 152 and/or the pressures within such regions may be generated based on model 113A and/or aligned (e.g. 3D) model 116A. Beam simulations may be performed with suitable software, such as Sim4Life™ commercialized by Zurich MedTech and/or other suitable simulation software.

Method 100 may then optionally proceed to optional block 142 which involves an inquiry into whether the determined treatment focus location 138 is acceptable. The block 142 inquiry may be performed by a human operator (who may have access to the block 140 display/image), by a suitably configured processor or controller (e.g. controller 14 associated with ultrasound therapy system 10) or by both a human operator and a suitably configured processor or controller. Block 140 may involve a comparison between determined treatment focus location 138 and a desired treatment focus location for patient 1. As discussed above, such a desired treatment focus location may be determined for a particular ultrasound treatment within treatment plan 118A in the block 110 preparation process.

The block 142 inquiry may involve ascertaining whether determined treatment focus location 138 is within a configurable error threshold relative to the desired treatment focus location (e.g. within a threshold distance of the desired focus location). The block 142 error threshold may be any suitable value. For example, the error threshold may be 1 mm, 5 mm, 1 cm, 5 cm, etc. The error threshold may be determined as a fraction of the wavelength used in the treatment transmission. For example, for a frequency of 220 kHz, the wavelength is about 7 mm. Thus, for an approximate allowable error of ¼ of a wavelength, the threshold can be set to 2 mm.

If the block 142 inquiry determines that determined treatment focus location 138 is acceptable (block 142 YES branch), then method 100 may proceed to optional block 144, where ultrasound treatment may proceed (e.g. using transmit transducers 12A at suitable treatment power (or other treatment parameter), which will generally be higher (or otherwise different) than the corresponding power (or other treatment parameter) of pre-treatment transmission of block 128). If, on the other hand, the block 142 inquiry determines that the determined treatment focus location 138 is not acceptable, then method 100 may proceed to optional block 146 which involves making one or more adjustments which may impact the treatment focus location of ultrasound therapy system 10. By way of non-limiting example, the types of adjustment(s) which may be made in block 146 may comprise: adjustment of model 113A, adjustment of the location of cap 11 (or determination of the location of cap 11) relative to head 1A of patient 1, adjustment of the locations of one or more transducers 12 (or determination of the locations of one or more transducers 12) within cap 11, adjustment of a suitable subset of transmit transducers 12A in cap 11 which may be selected for use in treatment, adjustment of assumed velocities or velocity profiles, and/or the like.

After making adjustments in block 146, method 100 may loop back to block 110 for another iteration of method 100 with the block 146 adjustments. It will be appreciated that with the block 146 adjustments, subsequent iterations of method 100 will determine a new treatment focus location 138.

Figure 3:
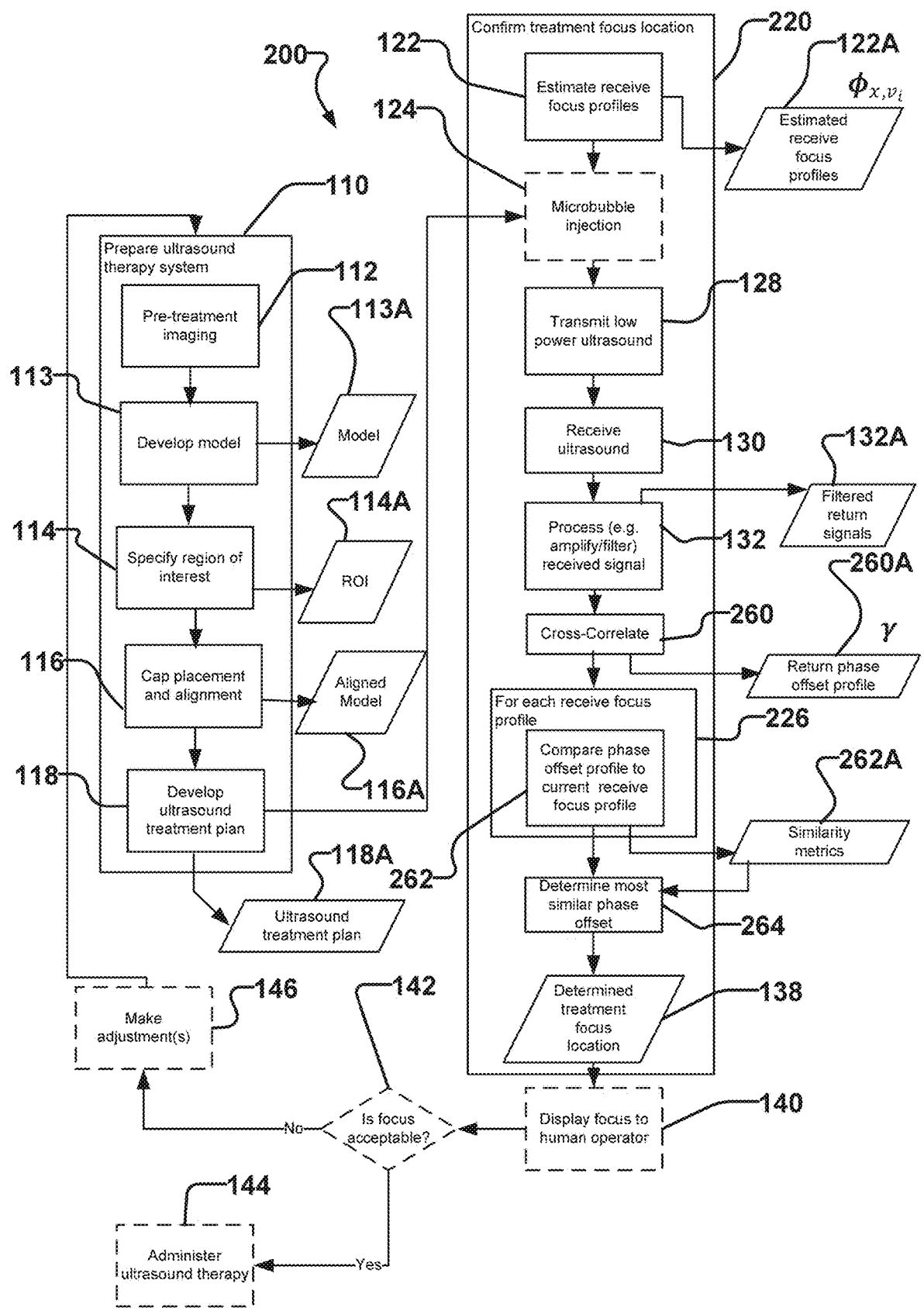
FIG. 3 is a flow chart of an example method for the confirmation of treatment focus location of ultrasound according to particular embodiment.

FIG. 3 is a flow chart of an example method 200 for the confirmation of the treatment focus location of ultrasound according to another particular embodiment. In many respects, method 200 is similar to method 100 and similar reference numerals are used to represent similar features. This description focuses on the differences between method 200 and method 100. In other respects, method 200 should be considered to be similar to (and include any variations or modifications to) method 100. Block 110 (including blocks 112, 113, 114, 116, 118 and their outputs) of method 200 is substantially similar to block 110 of method 100. The block 220 confirmation of treatment focus procedure and loop 226 of method 200 differ in some respects from the block 120 confirmation of treatment focus procedure and loop 126 of method 100. The block 220 confirmation of treatment focus procedure of method 200 starts with blocks 122, 124 and 128 that are similar to blocks 122, 124 and 128 of block 120.

The block 220 confirmation of treatment focus procedure of the FIG. 3 method 200 then proceeds to blocks 130 and 132 which are similar to blocks 130 and 132 of method 100 and involve receiving return (e.g. reflected) ultrasound signals at each of N receive transducers 12B (in block 130) and processing (e.g. amplifying and filtering) the block 130 received signals (in block 132). As discussed above, block 132 may comprise extracting a fundamental (first harmonic) or higher order harmonic (e.g. a $2^{nd}$ order harmonic, a $3^{rd}$ order harmonic or some other higher order (non-fundamental) harmonic) of the block 128 transmit frequency. The signals extracted from block 132 are shown as filtered return signals 132A in FIG. 3.

The block 220 confirmation of treatment focus procedure of the FIG. 3 method 200 then proceeds to block 260 which involves performing a cross-correlation operation of filtered return signals 132A from each of the N receive transducers 12B with the filtered return signal 132A from the receive transducer 12B that, in the illustrated embodiment, was designated in block 122 to be the reference transducer (n*). For each of the N receive transducers 12B, the block 260 cross-correlation operation determines a phase offset (or time offset) of the filtered return signals 132A relative to the filtered return signal 132A corresponding to reference transducer (n*). For each of the N receive transducers 12B, this phase offset (or time offset) may be referred to herein as a cross-correlation parameter $\gamma_n$, where the subscript refers to the $n^{th}$ receive transducer 12B. The cross-correlation parameter $\gamma_{n^*}$ for the reference transducer (n*) may be $\gamma_{n^*}=0$. In some embodiments, rather than cross-correlating the filtered return signals 132A for each of the N receive transducers 12B against the filtered return signal 132A of a single reference transducer (n*), the block 260 cross-correlation may be performed between the filtered return signals 132A of neighboring (e.g. nearest neighbor) receive transducers 12B to obtain a phase offset (or time offset) of the filtered return signals 132A between such neighboring receive transducers 12B. Then, these phase offsets (or time offsets) can be referenced back to a single reference transducer (n*) to generate the cross-correlation parameter $\gamma_n$. For example, if the phase offset (determined by cross-correlation) between the filtered return signals 132A of neighboring receive transducers n* and n=1 is $\psi_{*,1}$, the phase offset (determined by cross-correlation) between the filtered return signals 132A of neighboring receive transducers n=2 and n=1 is $\psi_{1,2}$ and the phase offset (determined by cross-correlation) between the filtered return signals 132A of neighboring receive transducers n=3 and n=2 is $\psi_{2,3}$, then the cross-correlation parameter $\gamma_1$ (i.e. for the receive transducer n=1 relative to the reference receive transducer n*) may be $\gamma_1=\psi_{*,1}$, the cross-correlation parameter $\gamma_2$ (i.e. for the receive transducer n=2 relative to the reference receive transducer n*) may be $\gamma_2=\psi_{*,1}+\psi_{1,2}$, the cross-correlation parameter $\gamma_3$ (i.e. for the receive transducer n=3 relative to the reference receive transducer n*) may be $\gamma_3=\psi_{*,1}+\psi_{*,1}+\psi_{1,2}+\psi_{2,3}$ and so on.

Typically, the block 260 cross-correlation operation is carried out in the digital sampled domain. Part of the block 260 cross-correlation may comprise determining a number of samples that each filtered return signal 132A should be advanced or retarded with respect to the filtered return signal 132A corresponding to a reference transducer (n*). This number of samples may be converted to a phase (or time) equivalent. Conversion from the sample domain to phase or time domain in block 260 may be based on the analog to digital sampling rate, any potential up sampling or down sampling of the signals in the digital domain and a determined number of digital samples per unit wavelength of the filtered return signal 132A being analyzed at the frequency of interest (e.g. a higher order harmonic of the proposed treatment frequency). For example, if the frequency of interest after filtering in block 132 is 440 kHz (e.g. second harmonic of an example treatment frequency of 220 kHz), then the wavelength would be 3.5 mm based on a velocity of sound 1540 m/s. Also for the frequency of 440 kHz, the period is 2.27 ms. A typical sampling frequency is 4 times the frequency; so, in the sample domain, the samples may be 0.56 ms apart, which translates to an equivalent phase of $\pi/2$. Thus $\gamma_n$ may be expressed as phase or time-based values (phase offsets or time offsets) as appropriate.

The reference transducer (n*) used in block 260 may be the same reference transducer (n*) used to determine the receive focus profiles $\phi_{x,v_i}$ (122A) in block 122. Accordingly, block 122 may involve storing the identity of the reference transducer (n*) for receive focus profiles $\phi_{x,v_i}$ (122A).

The collection of cross-correlation parameters $\gamma_n$ for each of the N receive transducers may be referred to herein as a return phase offset profile $\gamma$ (260A), where $\gamma$ is a N dimensional quantity and each element of the return phase offset profile $\gamma$ (260A) comprises a cross-correlation parameter $\gamma_n$ for a corresponding receive transducer 12B that may be determined using the same reference transducer (n*) used to determine receive focus profiles $\phi_{x,v_i}$ (122A).

Block 220 then proceeds to a loop 226 which is performed once for each receive focus profile $\phi_{x,v_i}$. Each iteration of loop 226 comprises block 262 which involves comparing the phase offset profile $\gamma$ (260A) to the current receive focus profile $\phi_{x,v_i}$ (122A) to determine a similarity metric 262A as between the phase offset profile $\gamma$ (260A) and the current receive focus profile $\phi_{x,v_i}$ (122A). As part of loop 226, block 262 is performed for each receive focus profile $\phi_{x,v_i}$ (122A) and as such will involve a comparison of the phase offset profile $\gamma$ (260A) and a receive focus profile $\phi_{x,v_i}$ (122A) determined using the same reference transducer (n*). The block 220 comparison may comprise performing an element-by-element similarity assessment of the N cross-correlation parameters $\gamma_n$ of phase offset profile $\gamma$ (260A) to the N phase offsets $\phi_{x,v_i}^n$ of the current receive focus profile $\phi_{x,v_i}$. By way of non-limiting example, the block 262 similarity assessment may comprise: subtracting each cross-correlation parameter $\gamma_n$ from the corresponding phase offset value ox of the current receive focus profile $\phi_{x,v_i}$; taking the absolute value (or the square) of the N resultant differences; and summing the absolute value (or the square) over the N transducers to determine a similarity metric 262A for the current receive focus profile $\phi_{x,v_i}$. It will be appreciated that, with this block 262 similarity assessment technique, a smaller similarity metric 262A is indicative of a greater similarity between the phase offset profile $\gamma$ (260A) and the current receive focus profile $\phi_{x,v_i}$ (122A). As an example, if all elements the phase offset profile $\gamma$ (260A) and the current receive focus profile $\phi_{x,v_i}$ (122A) were the same, then the similarity metric 262A determined using this technique would be 0.

In some embodiments, the block 262 determination of similarity metric 262A as between the phase offset profile $\gamma$ (260A) and the current receive focus profile $\phi_{x,v_i}$ (122A) may comprise any additional or alternative technique for assessing a relative similarity between two N-dimensional vectors.

Method 200 exits loop 226 when similarity metrics 262A have been generated for each of the receive focus profiles $\phi_{x,v_i}$ (122A) generated in block 120. The number of similarity metrics 262A will be the same as the number of receive focus profiles $\phi_{x,v_i}$, which is product of the number X of candidate treatment focus locations x and the number I of assumed ultrasound velocity profiles $v_i$ for each candidate treatment focus location x.

After loop 226, method 200 proceeds to block 264 which involves determining the confirmed treatment focus location 138 to be the location x corresponding to the receive focus profile $\phi_{x,v_i}$ for which the similarity metric 262A is the lowest (or is otherwise indicative of the highest degree of similarity) from among the set of similarity metrics 262A. If there are two or more receive focus profiles $\phi_{x,v_i}$ that are maximally similar to their corresponding phase offset profile $\gamma$ (260A), then a suitable technique may be used to select a determined treatment focus location 138 based on the two or more maximally similar receive focus profiles $\phi_{x,v_i}$. By way of non-limiting example, such a technique may comprise: allowing a user to select one of the locations x of the two or more maximally similar receive focus profiles $\phi_{x,v_i}$; averaging the locations x of the two or more maximally similar receive focus profiles $\gamma$ and/or the like. In some embodiments, where there are two or more receive focus profiles $\phi_{x,v_i}$ that are maximally similar to their corresponding phase offset profile $\gamma$ (260A), method 200 may output a message or other output indicating that the treatment focus location confirmation was not successful, that treatment ultrasound energy should not be delivered to the patient because the treatment focus location could not be confirmed and/or the like.

In some embodiments, block 264 may comprise outputting the determined treatment focus location 138 (e.g. in a format that is suitable for interpretation by a human operator and/or by a suitable processor (e.g. a processor (not shown) associated with ultrasound therapy system 10). In some embodiments, the output of determined treatment focus location 138 (as part of block 264 or otherwise) may conclude method 200—i.e. method 200 may be complete with the output of determined treatment focus location 138. As discussed above in relation to method 100, the treatment focus confirmation of block 220 may be performed for each ultrasound treatment (and each corresponding treatment focus location) within treatment plan 118A. As such, method 200 may conclude after a number of iterations of treatment focus confirmation block 220 and a number of determined treatment focus locations 138.

The remaining steps of method 200 may be optional and may be performed in some embodiments. Although only shown once in the illustrated embodiment of FIG. 3, the remaining steps of method 200 may be performed for each determined treatment focus location 138. These optional steps (including blocks 140, 142, 144 and 146) of method 200 may be substantially similar to those described above in connection with method 100.

Figure 5:
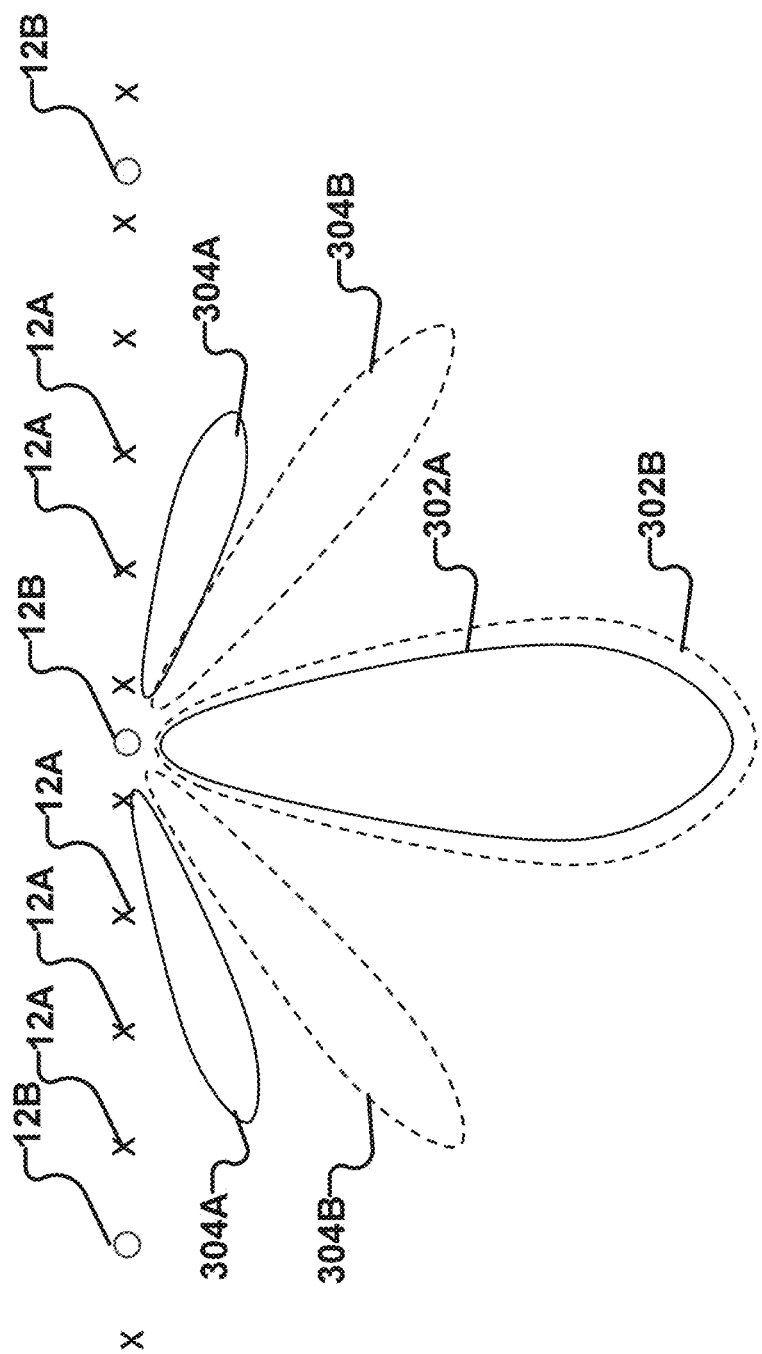
FIG. 5 is a schematic of a number of transmit transducers and receive transducers according to a particular embodiment which may be part of any of the other ultrasound therapy systems described herein together with a schematic depiction of the beam pattern that may be obtained from an array of transducers.

FIG. 5 is a schematic of a number of transmit transducers 12A and receive transducers 12B according to a particular embodiment which may be part of ultrasound therapy system 10 or any of the other ultrasound therapy systems described herein. FIG. 5 schematically illustrates the beam pattern that may be obtained from an array of transducers. Beam patterns are typically described as having "lobes" such as the main lobe, side lobe, grating lobes etc. A lobe is where the sensitivity is high for that particular array configuration, whether the transducer array is in transmit mode or receive mode. In the FIG. 5 illustration, main lobe 302A and grating lobes 304A of transmit transducers 12A are shown in solid lines and the main lobe 302B and grating lobes 304B of receive transducers 12B are shown in dashed lines. As is known in the art, grating lobes 304A, 304B arise because of spacing between transducers 12A and between transducers 12B. Larger spacings (for example, between transducers 12B) results in grating lobes 304B occurring closer to main lobes 302B. Smaller spacings (for example, between transducers 12A) results in grating lobes 304A occurring further away from main lobe 302A. It is not always practical to space transducers 12A or transducers 12B close enough to eliminate grating lobes (or to locate grating lobes outside of the head 1A of patient 1) because of the cost, complexities, computational expense etc. of adding additional transducers.

Treatment focal location ambiguity can arise in circumstances where main lobe 302A (from transmit transducers 12A) overlaps with grating lobes 304B (of receive transducers 12B). In the FIG. 5 configuration, receive transducers 12B are placed at different locations than transmit transducers 12A and the spacing of receive transducers 12B is larger than the spacing of transmit transducers 12A. The number of receive transducers 12B may also be fewer than the number of transmit transducers 12B. It is possible that the spacing of receive transducers 12B is such that receive grating lobes 304B form within head 1A of patient 1 (e.g. where the spacing of receive transducers 12B is $>=\lambda/2$, where $\lambda$ is the wavelength of interest). If the transmit frequency is at 220 kHz, for example, then $\lambda$ is approximately 7 mm. In the case of the second harmonic, $\lambda$ is approximately 3.5 mm.

Notably, for certain configurations such as shown in FIG. 5, the spacing and location of receive transducers 12B is different than for transmit transducers 12A and, consequently, the grating lobes 304A, 304B from transmit transducers 12A and receive transducers 12B do not overlap, while main lobes 302A, 302B from transmit transducers 12A and receive transducers 12B do desirably overlap. Thus, although at first review, the use of a relatively small number of spaced apart receive transducers 12B to confirm the treatment focus location of transmit transducers 12A (or of the treatment ultrasound energy) may appear to result in position ambiguity of the treatment focus location due the existence of grating lobes 304A, 304B, since only the main lobes 302A, 302B overlap, the FIG. 5 configuration is practical.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Software and other modules may reside on servers, workstations, personal computers, tablet computers, image data encoders, image data decoders, PDAs, color-grading tools, video projectors, audio-visual receivers, displays (such as televisions), digital cinema projectors, media players, and other devices suitable for the purposes described herein. Those skilled in the relevant art will appreciate that aspects of the system can be practised with other communications, data processing, or computer system configurations, including: Internet appliances, hand-held devices (including personal digital assistants (PDAs)), wearable computers, all manner of cellular or mobile phones, multi-processor systems, microprocessor-based or programmable consumer electronics (e.g., video projectors, audio-visual receivers, displays, such as televisions, and the like), set-top boxes, color-grading tools, network PCs, mini-computers, mainframe computers, and the like.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible). Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible). This is the case even if features A and B are illustrated in different drawings and/or mentioned in different paragraphs, sections or sentences.

Aspects of the Invention

The invention has a number of non-limiting aspects. Non-limiting aspects of the invention include:

1. A method for confirming a treatment characteristic of an ultrasound therapy system, the ultrasound therapy system comprising a plurality of transmit transducers for transmitting ultrasound energy into the brain of a patient and a plurality of receive transducers for receiving reflected ultrasound energy from the brain of the patient, the method comprising:
    obtaining a proposed ultrasound treatment parameterized by, for each of the plurality of transmit transducers, treatment values for a corresponding plurality of transmission parameters;
    transmitting pre-treatment ultrasound energy into the brain of the patient, wherein transmitting the pre-treatment ultrasound energy comprises causing each of the plurality of transmit transducers to transmit ultrasound energy according to pre-treatment values for the corresponding plurality of transmission parameters, wherein the pre-treatment values for a first one or more of the corresponding plurality of transmission parameters are different than the treatment values for the first one or more of the corresponding plurality of transmission parameters and the pre-treatment values for a second one or more of the corresponding plurality of transmission parameters are the same as the treatment values for the second one or more of the corresponding plurality of transmission parameters;
    receiving return pre-treatment signals at the plurality of receive transducers; and
    determining the treatment characteristic based at least in part on the received return pre-treatment signals.
2. The method of aspect 1 or any other aspect herein wherein the treatment characteristic is a treatment focus location of the proposed ultrasound treatment.
3. The method of any one of aspects 1 to 2 or any other aspect herein wherein the first one or more of the corresponding plurality of transmission parameters is one of the corresponding plurality of transmission parameters.
4. The method of any one of aspects 1 to 3 or any other aspect herein wherein the first one or more of the corresponding plurality of transmission parameters comprises a power of the ultrasound transmission by the transmit transducer.
5. The method of aspect 4 or any other aspect herein wherein the pre-treatment value of the power is less than the treatment value of the power.
6. The method of any one of aspects 1 to 3 or any other aspect herein wherein the first one or more of the corresponding plurality of transmission parameters comprises a pulse length of the ultrasound transmission by the transmit transducer.
7. The method of aspect 6 or any other aspect herein wherein the pre-treatment value of the pulse length is less than the treatment value of the pulse length.
8. The method of any one of aspects 1 to 7 or any other aspect herein comprising at least one of: injecting microbubbles into the patient before transmitting pre-treatment ultrasound energy into the brain of the patient; and injecting microbubbles into the patient during at least a portion of transmitting pre-treatment ultrasound energy into the brain of the patient.

9. The method of any one of aspects 1 to 8 or any other aspect herein comprising filtering the return pre-treatment signals to extract filtered return signals, each filtered return signal corresponding to one of the plurality of receive transducers and wherein determining the treatment characteristic based at least in part on the received return pre-treatment signals comprises determining the treatment characteristic based at least in part on the filtered return signals.

10. The method of aspect 9 or any other aspect herein wherein the second one or more of the corresponding plurality of transmission parameters comprises a treatment frequency of the ultrasound transmission by the transmit transducer.

11. The method of aspect 10 or any other aspect herein wherein filtering the return pre-treatment signals to extract filtered return signals comprises band-pass filtering the return pre-treatment signals to extract, as the filtered return signals, one of: a fundamental (first harmonic) of the treatment frequency; and a higher order (e.g. $2^{nd}$ or higher order) harmonic of the treatment frequency.

12. The method of any one of aspects 1 to 7 or any other aspect herein comprising:
   at least one of: injecting microbubbles into the patient before transmitting pre-treatment ultrasound energy into the brain of the patient; and injecting microbubbles into the patient during at least a portion of transmitting pre-treatment ultrasound energy into the brain of the patient; and
   filtering the return pre-treatment signals to extract filtered return signals, each filtered return signal corresponding to one of the plurality of receive transducers and wherein determining the treatment characteristic based at least in part on the received return pre-treatment signals comprises determining the treatment characteristic based at least in part on the filtered return signals;
   wherein the second one or more of the corresponding plurality of transmission parameters comprises a treatment frequency of the ultrasound transmission by the transmit transducer; and
   wherein filtering the return pre-treatment signals to extract filtered return signals comprises band-pass filtering the return pre-treatment signals to extract, as the filtered return signals, a higher order (e.g. $2^{nd}$ or higher order) harmonic of the treatment frequency.

13. The method of any of aspects 1 to 12 or any other aspect herein wherein the treatment characteristic is a treatment focus location of the proposed ultrasound treatment and wherein the method comprises:
   determining a plurality of receive focus profiles $\phi_{x,v_i}$;
       each receive focus profile $\phi_{x,v_i}$ corresponding to a candidate treatment focus location x from among a plurality of X candidate locations and corresponding to an assumed ultrasound propagation velocity profile $v_i$ from among a plurality of I of assumed ultrasound propagation velocity profiles, and
       each receive focus profile $\phi_{x,v_i}$ comprising N elements $\phi_{x,v_i}^n$ where N corresponds to a number of the plurality of receive transducers and the element $\phi_{x,v_i}^n$ comprises a phase offset or a time offset for an $n^{th}$ one of the plurality of receive transducers; and
   wherein determining the plurality of receive focus profiles $\phi_{x,v_i}$ comprises, for each of the plurality of receive focus profiles $\phi_{x,v_i}$, determining the phase offset or the time offset $\phi_{x,v_i}^n$ based on the candidate treatment focus location x, a location of the $n^{th}$ receive transducer relative to the treatment focus location x and the assumed velocity profile $v_i$; and
   wherein determining the treatment characteristic based at least in part on the received return pre-treatment signals comprises determining the treatment focus location based at least in part on the received return pre-treatment signals and the receive focus profiles $\phi_{x,v_i}$.

14. The method of aspect 13 or any other aspect herein wherein determining the treatment focus location based at least in part on the received return pre-treatment signals and the receive focus profiles $\phi_{x,v_i}$ comprises:
   filtering the received return pre-treatment signals to extract filtered return signals, each filtered return signal corresponding to one of the receive transducers; and
   determining the treatment focus location based at least in part on the filtered return signals and the receive focus profiles $\phi_{x,v_i}$.

15. The method of aspect 14 or any other aspect herein wherein:
   the second one or more of the corresponding plurality of transmission parameters comprises a treatment frequency of the ultrasound transmission by the transmit transducer;
   filtering the received return pre-treatment signals to extract filtered return signals comprises filtering the received return pre-treatment signals using band pass filters; and
   the band-pass filters are configured to extract, as the filtered return signals, one of: a fundamental (first harmonic) of the treatment frequency; and a higher order (e.g. $2^{nd}$ or higher order) harmonic of the treatment frequency.

16. The method of aspect 15 or any other aspect herein wherein determining the plurality of receive focus profiles $\phi_{x,v_i}$ comprises determining each of the plurality of receive focus profiles $\phi_{x,v_i}$ at a focus-profile frequency that corresponds to the one of: the fundamental (first harmonic) of the treatment frequency; and the higher order (e.g. $2^{nd}$ or higher order) harmonic of the treatment frequency.

17. The method of any one of aspects 15 to 16 or any other aspect herein wherein:
   the method comprises at least one of: injecting microbubbles into the patient before transmitting pre-treatment ultrasound energy into the brain of the patient; and during at least a portion of transmitting pre-treatment ultrasound energy into the brain of the patient;
   the band-pass filters are configured to extract, as the filtered return signals, a higher order (e.g. $2^{nd}$ or higher order) harmonic of the treatment frequency.

18. The method of aspect 17 or any other aspect herein wherein determining the plurality of receive focus profiles $\phi_{x,v_i}$ comprises determining each of the plurality of receive focus profiles $\phi_{x,v_i}$ at a focus-profile frequency that corresponds to the higher order (e.g. $2^{nd}$ or higher order) harmonic of the treatment frequency.

19. The method of any one of aspects 14 to 18 or any other aspect herein wherein determining the treatment focus location based at least in part on the filtered return signals and the receive focus profiles $\phi_{x,v_i}$ comprises:
   for each receive focus profile $\phi_{x,v_i}$: applying the receive focus profile $\phi_{x,v_i}$ to the filtered return signals to determine phase-adjusted signals or time-adjusted signals; and summing the phase-adjusted signals or time-adjusted signals to determine a sum signal $S_{x,v_i}$ corresponding to the receive focus profile $\phi_{x,v_i}$; and determining the focus location based at least in part on the sum signals $S_{x,v_i}$ corresponding to the plurality of receive focus profiles $\phi_{x,v_i}$.

20. The method of aspect 19 or any other aspect herein wherein applying the receive focus profile $\phi_{x,v_i}$ to the filtered return signals to determine phase-adjusted signals or time-adjusted signals comprises, for each filtered return signal, adjusting a phase of the filtered return signal by the phase offset of a corresponding element $\phi_{x,v_i}^n$ of the receive focus profile $\phi_{x,v_i}$ to thereby determine a corresponding phase-adjusted signal or adjusting a time of the filtered return signal by the time offset of a corresponding element $\phi_{x,v_i}^n$ of the receive focus profile $\phi_{x,v_i}$ to thereby determine a corresponding time-adjusted signal.

21. The method of any one of aspects 19 to 20 or any other aspect herein wherein determining the treatment focus location based at least in part on the sum signals $S_{x,v_i}$ corresponding to the plurality of receive focus profiles $\phi_{x,v_i}$ comprises: extracting a value $S_{x,v_i}^l$ from each sum signal $S_{x,v_i}$; and determining the treatment focus location based on the extracted values $S_{x,v_i}^l$.

22. The method of aspect 21 or any other aspect herein wherein extracting a value $S_{x,v_i}^l$ from each sum signal $S_{x,v_i}$ comprises at least one of: integrating the sum signal $S_{x,v_i}$ corresponding to the receive focus profile $\phi_{x,v_i}$ to obtain the extracted value $S_{x,v_i}^l$ corresponding to the receive focus profile $\phi_{x,v_i}$; and extracting a maximum magnitude value from the sum signal $S_{x,v_i}$ corresponding to the receive focus profile $\phi_{x,v_i}$ to obtain the extracted value $S_{x,v_i}^l$ corresponding to the receive focus profile $\phi_{x,v_i}$.

23. The method of any one of aspects 21 to 22 or any other aspect herein wherein determining the treatment focus location based on the extracted values $S_{x,v_i}^l$ comprises determining the treatment focus location to be the candidate treatment focus location x corresponding to the receive focus profile $\phi_{x,v_i}$ having the largest extracted value $S_{x,v_i}^l$ from among the extracted values corresponding to the plurality of receive focus profiles $\phi_{x,v_i}$.

24. The method of any one of aspects 14 to 18 or any other aspect herein wherein determining the treatment focus location based at least in part on the filtered return signals and the receive focus profiles $\phi_{x,v_i}$ comprises:
cross-correlating each of the filtered return signals with a reference one of the filtered return signals or another one (e.g. a nearest neighbor of the plurality of receive transducers) of the filtered return signals to obtain a return phase offset or time offset profile $\gamma$, where the return phase offset or time offset profile $\gamma$ comprises one cross-correlation parameter $\gamma_n$ for each of the plurality of receive transducers, the cross-correlation parameter $\gamma_n$ indicative of a phase offset or time offset of the $n^{th}$ filtered return signal relative to the reference filtered return signal; and
determining the treatment focus location based at least in part on the return phase offset or time offset profile $\gamma$ and the plurality of receive focus profiles $\phi_{x,v_i}$.

25. The method of aspect 24 or any other aspect herein wherein the reference one of the filtered return signals used to obtain the return phase offset or time offset profile $\gamma$ corresponds to the filtered return signal from a reference one of the plurality of receive transducers used for determining the receive focus profile $\phi_{x,v_i}$.

26. The method of any one of aspects 24 to 25 or any other aspect herein wherein determining the treatment focus location based at least in part on the return phase offset or time offset profile $\gamma$ and the plurality of receive focus profiles $\phi_{x,v_i}$ comprises: for each receive focus profile $\phi_{x,v_i}$, comparing the return phase offset or time offset profile $\gamma$ to the focus profile $\phi_{x,v_i}$ to obtain a corresponding similarity metric as between the return phase offset or time offset profile $\gamma$ and the receive focus profile $\phi_{x,v_i}$; and determining the focus location based on the similarity metrics for the plurality of receive focus profiles $\phi_{x,v_i}$.

27. The method of aspect 26 or any other aspect herein wherein determining the treatment focus location based on the similarity metrics for the plurality of receive focus profiles $\phi_{x,v_i}$ comprises determining the treatment focus location to be at the candidate treatment focus location x of the receive focus profile $\phi_{x,v_i}$ that is most similar to the return phase offset or time offset profile $\gamma$.

28. The method of any one of aspects 13 to 27 or any other aspect herein wherein determining the phase offset or time offset for each element $\phi_{x,v_i}^n$ is based on a physical and acoustic model of the head of the patient to be treated by the ultrasound therapy system.

29. The method of aspect 28 or any other aspect herein wherein determining the phase offset or time offset for each element $\phi_{x,v_i}^n$ is based on at least one of: an estimated locations of the $n^{th}$ receive transducer; and an estimated position of a structure (e.g. a cap) which supports the receive transducers relative to the head of the patient.

30. The method of any one of aspects 13 to 27 or any other aspect herein wherein determining the phase offset or time offset for each element $\phi_{x,v_i}^n$ is based on an aligned model which specifies a physical and acoustic model of the head of the patient to be treated by the ultrasound therapy system and alignment between the model and at least one of: an estimated position of the $n^{th}$ receive transducer; and an estimated position of a structure (e.g. a cap) which supports the receive transducers relative to the head of the patient.

31. The method of any one of aspects 28 to 30 or any other aspect herein wherein determining the phase offset or time offset for each element $\phi_{x,v_i}^n$ comprises:
selecting one ($n^*$) of the plurality of receive transducers to be a reference transducer; and
for each element $\phi_{x,v_i}^n$ corresponding to an $n^{th}$ one of the plurality of receive transducers:
determining a phase or time $\psi_{x,v_i}^n$ of an ultrasound wave that would be received at the $n^{th}$ one of the plurality of receive transducers with the velocity profile $v_i$ from the candidate treatment focus location x based on a simulation of ultrasound propagation between the candidate treatment focus location x and the $n^{th}$ one of the plurality of receive transducers based on the velocity profile $v_i$; and
determining $\phi_{x,v_i}^n$ to be a phase offset or time offset between the determined phase or time $\psi_{x,v_i}^n$ for the $n^{th}$ one of the plurality of receive transducers and the determined phase or time $\psi_{x,v_i}^{n^*}$ of the reference transducer according to $\phi_{x,v_i}^n = \psi_{x,v_i}^n - \psi_{x,v_i}^{n^*}$).

32. The method of any one of aspects 13 to 31 or any other aspect herein comprising graphically displaying the determined treatment focus location in an image of the brain of the patient.

33. The method of aspect 32 or any other aspect herein wherein graphically displaying the determined treatment focus location comprises graphically displaying one or more of:
a region of interest in the brain of the patient;
a desired treatment focus location of the proposed ultrasound treatment; and
a beam simulation of the ultrasound treatment based on the determined treatment focus location wherein the beam simulation is performed with, for each of the plurality of transmit transducers, at least a subset of the treatment values for the corresponding plurality of transmission parameters.

34. The method of aspect 33 or any other aspect herein wherein graphically displaying the determined treatment focus location comprises graphically displaying the beam simulation and wherein the beam simulation includes one or more regions (e.g. 0 to −3 dB; −3 bB to −6 dB and/or the like) of ultrasound pressure (e.g. peak-negative pressure) relative to ultrasound pressure at the determined treatment focus location.

35. The method of any one of aspects 32 to 34 or any other aspect herein wherein graphically displaying the determined treatment focus location comprises displaying the determined treatment focus location in a three-dimensional representation of the brain of the patient.

36. The method of any one of aspects 1 to 35 or any other aspect herein comprising, if the determined treatment characteristic is confirmed to be within a threshold similarity metric of the treatment characteristic, delivering ultrasound according to the proposed ultrasound treatment to open a blood brain barrier of the patient.

37. The method of any one of aspects 1 to 36 or any other aspect herein wherein the plurality of transmission parameters comprise beam-forming parameters.

38. A method for delivering ultrasound therapy using an ultrasound therapy system, the ultrasound therapy system comprising a plurality of transmit transducers for transmitting ultrasound energy into the brain of a patient and a plurality of receive transducers for receiving reflected ultrasound energy from the brain of the patient, the method comprising:
determining a desired treatment characteristic for treatment ultrasound energy to be delivered to the brain of the patient from the transmit transducers;
confirming the treatment characteristic according to any of the methods of any of aspects 1 to 37;
delivering the treatment ultrasound energy to the brain of the patient from the transmit transducers only if the confirmed treatment characteristic is within a threshold similarity metric of the desired treatment characteristic.

39. An ultrasound therapy system comprising:
a plurality of transmit transducers for transmitting ultrasound energy into the brain of a patient;
a plurality of receive transducers for receiving reflected ultrasound energy from the brain of the patient; and
a controller, the controller configured to:
obtain a proposed ultrasound treatment parameterized by, for each of the plurality of transmit transducers, treatment values for a corresponding plurality of transmission parameters;
cause the transmit transducers to transmit pre-treatment ultrasound energy into the brain of the patient, wherein transmitting the pre-treatment ultrasound energy comprises causing each of the plurality of transmit transducers to transmit ultrasound energy according to pre-treatment values for the corresponding plurality of transmission parameters, wherein the pre-treatment values for a first one or more of the corresponding plurality of transmission parameters are different than the treatment values for the first one or more of the corresponding plurality of transmission parameters and the pre-treatment values for a second one or more of the corresponding plurality of transmission parameters are the same as the treatment values for the second one or more of the corresponding plurality of transmission parameters;
receive return pre-treatment signals received at the plurality of receive transducers; and
determine the treatment characteristic based at least in part on the received return pre-treatment signals.

40. The system of aspect 39 comprising any of the features of, and/or wherein the ultrasound therapy system and/or the controller is configured to perform any of the features of, any of aspects 1 to 38.

41. A method for confirming a treatment focus location of a proposed ultrasound treatment to be effected by an ultrasound therapy system, the ultrasound therapy system comprising a plurality of transmit transducers for transmitting ultrasound energy into the brain of a patient and a plurality of receive transducers for receiving reflected ultrasound energy from the brain of the patient, the method comprising:
determining a plurality of receive focus profiles $\phi_{x,v_i}$;
each receive focus profile $\phi_{x,v_i}$ corresponding to a candidate treatment focus location x from among a plurality of X candidate locations and corresponding to an assumed ultrasound propagation velocity profile $v_i$ from among a plurality of I of assumed ultrasound propagation velocity profiles, and
each receive focus profile $\phi_{x,v_i}$ comprising N elements $\phi_{x,v_i}^{n*}$, where N corresponds to a number of the plurality of receive transducers and the element $\phi_{x,v_i}^{n}$ comprises a phase offset or time offset for an $n^{th}$ one of the plurality of receive transducers; and
wherein determining the plurality of receive focus profiles $\phi_{x,v_i}$ comprises, for each of the plurality of receive focus profiles $\phi_{x,v_i}$, determining the phase offset or time offset for each element $\phi_{x,v_i}^{n}$ based on the candidate treatment focus location x, a location of the $n^{th}$ receive transducer relative to the treatment focus location x and the assumed velocity profile $v_i$;
transmitting pre-treatment ultrasound energy into the brain of the patient using the plurality of transmit transducers;
receiving return pre-treatment signals at the plurality of receive transducers, each return pre-treatment signal corresponding to one of the receive transducers; and
determining the treatment focus location based at least in part on the received return pre-treatment signals and the receive focus profiles $\phi_{x,v_i}$.

42. The method of aspect 41 or any other aspect herein wherein determining the treatment focus location based at least in part on the received return pre-treatment signals and the receive focus profiles $\phi_{x,v_i}$ comprises:
filtering the received return pre-treatment signals to extract filtered return signals, each filtered return signal corresponding to one of the receive transducers; and
determining the treatment focus location based at least in part on the filtered return signals and the receive focus profiles $\phi_{x,v_i}$.

43. The method of aspect 42 or any other aspect herein wherein:
transmitting pre-treatment ultrasound energy into the brain of the patient comprises transmitting ultrasound energy into the brain of the patient with a pre-treatment frequency that is the same as a treatment frequency proposed to be used by the ultrasound therapy system for the proposed ultrasound treatment;

filtering the received return pre-treatment signals to extract filtered return signals comprises filtering the received return pre-treatment signals using band pass filters; and the band-pass filters are configured to extract, as the filtered return signals, one of: a fundamental (first harmonic) of the treatment frequency; and a higher order (e.g. $2^{nd}$ or higher order) harmonic of the treatment frequency.

44. The method of aspect 43 or any other aspect herein wherein determining the plurality of receive focus profiles $\phi_{x,v_i}$ comprises determining each of the plurality of receive focus profiles $\phi_{x,v_i}$ at a focus-profile frequency that corresponds to the one of: the fundamental (first harmonic) of the treatment frequency; and the higher order (e.g. $2^{nd}$ or higher order) harmonic of the treatment frequency.

45. The method of any one of aspects 43 to 44 or any other aspect herein wherein:
the method comprises injecting microbubbles into the patient at least one of: before transmitting pre-treatment ultrasound energy into the brain of the patient; and during at least a portion of transmitting pre-treatment ultrasound energy into the brain of the patient;
the band-pass filters are configured to extract, as the filtered return signals, the higher order (e.g. $2^{nd}$ or higher order) harmonic of the treatment frequency.

46. The method of aspect 45 or any other aspect herein wherein determining the plurality of receive focus profiles $\phi_{x,v_i}$ comprises determining each of the plurality of receive focus profiles $\phi_{x,v_i}$ at a focus-profile frequency that corresponds to the higher order (e.g. $2^{nd}$ or higher order) harmonic of the treatment frequency.

47. The method of any one of aspects 42 to 46 or any other aspect herein wherein determining the treatment focus location based at least in part on the filtered return signals and the receive focus profiles $\phi_{x,v_i}$ comprises:
for each receive focus profile $\phi_{x,v_i}$: applying the receive focus profile $\phi_{x,v_i}$ to the filtered return signals to determine phase-adjusted signals or time-adjusted signals; and summing the phase-adjusted signals or time-adjusted signals to determine a sum signal $S_{x,v_i}$ corresponding to the receive focus profile $\phi_{x,v_i}$; and
determining the treatment focus location based at least in part on the sum signals $S_{x,v_i}$ corresponding to the plurality of receive focus profiles $\phi_{x,v_i}$.

48. The method of aspect 47 or any other aspect herein wherein applying the receive focus profile $\phi_{x,v_i}$ to the filtered return signals to determine phase-adjusted signals or time-adjusted signals comprises, for each filtered return signal, adjusting a phase of the filtered return signal by the phase offset of a corresponding element $\phi_{x,v_i}^n$ of the receive focus profile $\phi_{x,v_i}$ to thereby determine a corresponding phase-adjusted signal or adjusting a time of the filtered return signal by the time offset of a corresponding element $\phi_{x,v_i}^n$ of the receive focus profile $\phi_{x,v_i}$ to thereby determine a corresponding time-adjusted signal.

49. The method of any one of aspects 47 to 48 or any other aspect herein wherein determining the treatment focus location based at least in part on the sum signals $S_{x,v_i}$ corresponding to the plurality of receive focus profiles $\phi_{x,v_i}$ comprises: extracting a value $S_{x,v_i}^1$ from each sum signal $S_{x,v_i}$; and determining the treatment focus location on the extracted values $S_{x,v_i}^1$.

50. The method of any of aspect 49 or any other aspect herein wherein extracting a value $S_{x,v_i}^1$ from each sum signal $S_{x,v_i}$ comprises at least one of: integrating the sum signal $S_{x,v_i}$ corresponding to the receive focus profile $\phi_{x,v_i}$ to obtain an integrated extracted value $S_{x,v_i}^1$ corresponding to the receive focus profile $\phi_{x,v_i}$; and extracting a maximum magnitude value from the sum signal $S_{x,v_i}$ corresponding to the receive focus profile $\phi_{x,v_i}$ to obtain the extracted value $S_{x,v_i}^1$ corresponding to the receive focus profile $\phi_{x,v_i}$.

51. The method of any one of aspects 49 to 50 or any other aspect herein wherein determining the treatment focus location based on the extracted values $S_{x,v_i}^1$ comprises determining the treatment focus location to be the candidate treatment focus location x corresponding to the receive focus profile $\phi_{x,v_i}$ having the largest extracted value $S_{x,v_i}^1$ from among the extracted values corresponding to the plurality of receive focus profiles $\phi_{x,v_i}$.

52. The method of any one of aspects 42 to 46 or any other aspect herein wherein determining the treatment focus location based at least in part on the filtered return signals and the receive focus profiles $\phi_{x,v_i}$ comprises:
cross-correlating each of the filtered return signals with a reference one of the filtered return signals or another one (e.g. a nearest neighbor of the plurality of receive transducers) of the filtered return signals to obtain a return phase offset or time offset profile $\gamma$, where the return phase offset or time offset profile $\gamma$ comprises one cross-correlation parameter $\gamma_n$ for each of the plurality of receive transducers, the cross-correlation parameter $\gamma_n$ indicative of a phase offset or time offset of the $n^{th}$ filtered return signal relative to the reference filtered return signal; and
determining the treatment focus location based at least in part on the return phase offset or time offset profile $\gamma$ and the plurality of receive focus profiles $\phi_{x,v_i}$.

53. The method of aspect 52 or any other aspect herein wherein the reference one of the filtered return signals used to obtain the return phase offset or time offset profile $\gamma$ corresponds to the filtered return signal from a reference one of the plurality of receive transducers used for determining the receive focus profile $\phi_{x,v_i}$.

54. The method of any one of aspects 52 to 53 or any other aspect herein wherein determining the treatment focus location based at least in part on the return phase offset or time offset profile $\gamma$ and the plurality of receive focus profiles $\phi_{x,v_i}$ comprises: for each receive focus profile $\phi_{x,v_i}$, comparing the return phase offset or time offset profile $\gamma$ to the receive focus profile $\phi_{x,v_i}$ to obtain a corresponding similarity metric as between the return phase offset or time offset profile $\gamma$ and the receive focus profile $\phi_{x,v_i}$; and determining the focus location based on the similarity metrics for the plurality of receive focus profiles $\phi_{x,v_i}$.

55. The method of aspect 54 or any other aspect herein wherein determining the treatment focus location based on the similarity metrics for the plurality of receive focus profiles $\phi_{x,v_i}$ comprises determining the treatment focus location to be at the candidate treatment focus location x of the receive focus profile $\phi_{x,v_i}$ that is most similar to the return phase offset or time offset profile $\gamma$.

56. The method of any one of aspects 41 to 55 or any other aspect herein wherein determining the phase offset or time offset for each element $\phi_{x,v_i}^n$ is based on a physical and acoustic model of a head of the patient to be treated by the ultrasound therapy system.

57. The method of aspect 56 or any other aspect herein wherein determining the phase offset or time offset for each element $\phi_{x,v_i}^n$ is based on at least one of: an estimated position of the $n^{th}$ receive transducer; and an estimated position of a structure (e.g. a cap) which supports the receive transducers relative to the head of the patient.

58. The method of any one of aspects 41 to 55 or any other aspect herein wherein determining the phase offset or time offset for each element $\phi_{x,v_i}^n$ is based on an aligned model which specifies a physical and acoustic model of a head of the patient to be treated by the ultrasound therapy system and alignment between the model and at least one of: an estimated position of the $n^{th}$ receive transducer; and an estimated position of a structure (e.g. a cap) which supports the receive transducers relative to the head of the patient.

59. The method of any one of aspects 56 to 58 or any other aspect herein wherein determining the phase offset or time offset for each element $\phi_{x,v_i}^n$ comprises:
  selecting one (n*) of the plurality of receive transducers to be a reference transducer; and
  for each element $\phi_{x,v_i}^n$ corresponding to an $n^{th}$ one of the plurality of receive transducers:
    determining a phase or time $\psi_{x,v_i}^n$ of an ultrasound wave that would be received at the $n^{th}$ one of the plurality of receive transducers with the velocity profile $v_i$ from the candidate treatment focus location x based on a simulation of ultrasound propagation between the candidate treatment focus location x and the $n^{th}$ one of the plurality of receive transducers based on the velocity profile $v_i$; and
    determining $\phi_{x,v_i}^n$ to be a phase offset or time offset between the determined phase or time $\psi_{x,v_i}^n$ for the $n^{th}$ one of the plurality of receive transducers and the determined phase or time $\psi_{x,v_i}^{n*}$ of the reference transducer according to $\phi_{x,v_i}^{n*} = \psi_{x,v_i}^n - \psi_{x,v_i}^{n*}$)

60. A method according to any one of aspects 41 to 59 or any other aspect herein comprising injecting microbubbles into the patient at least one of: before transmitting pre-treatment ultrasound energy into the brain of the patient; and during at least a portion of transmitting pre-treatment ultrasound energy into the brain of the patient.

61. A method according to any one of aspects 41 to 60 or any other aspect herein wherein:
  the proposed ultrasound treatment is parameterized by, for each of the plurality of transmit transducers, treatment values for a corresponding plurality of transmission parameters
  transmitting pre-treatment ultrasound energy into the brain of the patient using the plurality of transmit transducers comprises causing each of the plurality of transmit transducers to transmit ultrasound energy according to pre-treatment values for the corresponding plurality of transmission parameters, wherein the pre-treatment values for a first one or more of the corresponding plurality of transmission parameters are different than the treatment values for the first one or more of the corresponding plurality of transmission parameters and the pre-treatment values for a second one or more of the corresponding plurality of transmission parameters are the same as the treatment values for the second one or more of the corresponding plurality of transmission parameters.

62. The method of aspect 61 or any other aspect herein wherein the first one or more of the corresponding plurality of transmission parameters is one of the corresponding plurality of transmission parameters.

63. The method of any one of aspects 61 to 62 or any other aspect herein wherein the first one or more of the corresponding plurality of transmission parameters comprises a power of the ultrasound transmission by the transmit transducer.

64. The method of aspect 63 or any other aspect herein wherein the pre-treatment value of the power is less than the treatment value of the power.

65. The method of any one of aspects 61 to 62 or any other aspect herein wherein the first one or more of the corresponding plurality of transmission parameters comprises a pulse length of the ultrasound transmission by the transmit transducer.

66. The method of aspect 65 or any other aspect herein wherein the pre-treatment value of the pulse length is less than the treatment value of the pulse length.

67. A method according to any one of aspects 61 to 66 or any other aspect herein wherein the second one or more of the corresponding plurality of transmission parameters comprises a frequency of the ultrasound transmission by the transmit transducer.

68. The method of any one of aspects 41 to 67 or any other aspect herein comprising graphically displaying the determined treatment focus location in an image of the brain of the patient.

69. The method of aspect 68 or any other aspect herein wherein graphically displaying the determined treatment focus location comprises graphically displaying one or more of:
  a region of interest in the brain of the patient;
  a desired treatment focus location of the proposed ultrasound treatment; and
  a beam simulation of the ultrasound treatment based on the determined treatment focus location wherein the beam simulation is performed with, for each of the plurality of transmit transducers, at least a subset of the treatment values for the corresponding plurality of transmission parameters.

70. The method of aspect 69 or any other aspect herein wherein graphically displaying the determined treatment focus location comprises graphically displaying the beam simulation and wherein the beam simulation includes one or more regions (e.g. 0 to −3 dB; −3 bB to −6 dB and/or the like) of ultrasound pressure (e.g. peak-negative pressure) relative to ultrasound pressure at the determined treatment focus location.

71. The method of any one of aspects 68 to 70 or any other aspect herein wherein graphically displaying the determined treatment focus location comprises displaying the determined treatment focus location in a three-dimensional representation of the brain of the patient.

72. The method of any one of aspects 41 to 71 or any other aspect herein comprising, if the determined treatment characteristic is confirmed to be within a threshold similarity metric of the treatment characteristic, delivering ultrasound according to the proposed ultrasound treatment to open a blood brain barrier of the patient.

73. The method of any one of aspects 41 to 72 or any other aspect herein wherein the plurality of transmission parameters comprise beam-forming parameters.

74. A method for delivering ultrasound therapy using an ultrasound therapy system, the ultrasound therapy system comprising a plurality of transmit transducers for transmitting ultrasound energy into the brain of a patient and a plurality of receive transducers for receiving reflected ultrasound energy from the brain of the patient, the method comprising:
  determining a desired treatment focus location for treatment ultrasound energy to be delivered to the brain of the patient from the transmit transducers;
  confirming a treatment focus location according to any of the methods of any of aspects 41 to 73;

delivering the treatment ultrasound energy to the brain of the patient from the transmit transducers only if the confirmed treatment focus location is within a threshold distance of the desired treatment focus location.
75. An ultrasound therapy system comprising:
a plurality of transmit transducers for transmitting ultrasound energy into the brain of a patient;
a plurality of receive transducers for receiving reflected ultrasound energy from the brain of the patient; and
a controller, the controller configured to:
determine a plurality of receive focus profiles $\phi_{x,v_i}$;
each receive focus profile $\phi_{x,v_i}$ corresponding to a candidate treatment focus location x from among a plurality of X candidate locations and corresponding to an assumed ultrasound propagation velocity profile $v_i$ from among a plurality of I of assumed ultrasound propagation velocity profiles, and
each receive focus profile $\phi_{x,v_i}$ comprising N elements $\phi_{x,v_i}^n$, where N corresponds to a number of the plurality of receive transducers and the element $\phi_{x,v_i}^n$ comprises a phase offset or time offset for an $n^{th}$ one of the plurality of receive transducers; and
wherein determining the plurality of receive focus profiles $\phi_{x,v_i}$ comprises, for each of the plurality of receive focus profiles $\phi_{x,v_i}$, determining the phase offset or time offset for each element on $\phi_{x,v_i}^n$ based on the candidate treatment focus location x and the assumed velocity profile $v_i$;
cause the transmit transducers to transmit pre-treatment ultrasound energy into the brain of the patient;
receive return pre-treatment signals received at the plurality of receive transducers, each return pre-treatment signal corresponding to one of the receive transducers; and
determine the treatment focus location based at least in part on the received return pre-treatment signals and the receive focus profiles $\phi_{x,v_i}$.
76. The system of aspect 75 comprising any of the features of, and/or wherein the controller is configured to perform any of the features of, any of aspects 41 to 74.
77. Apparatus having any new and inventive feature, combination of features, or sub-combination of features as described herein.
78. Methods having any new and inventive steps, acts, combination of steps and/or acts or sub-combination of steps and/or acts as described herein.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:
1. A method for confirming a treatment characteristic of an ultrasound therapy system, the ultrasound therapy system comprising a plurality of transmit transducers for transmitting ultrasound energy into the brain of a patient and a plurality of receive transducers for receiving reflected ultrasound energy from the brain of the patient, the method comprising:

obtaining a proposed ultrasound treatment parameterized by, for each of the plurality of transmit transducers, treatment values for a corresponding plurality of transmission parameters;
transmitting pre-treatment ultrasound energy into the brain of the patient, wherein transmitting the pre-treatment ultrasound energy comprises causing each of the plurality of transmit transducers to transmit ultrasound energy according to pre-treatment values for the corresponding plurality of transmission parameters, wherein:
the pre-treatment value for a transmission power is different than the treatment value for the transmission power, and
the pre-treatment values for a second one or more of the corresponding plurality of transmission parameters are the same as the treatment values for the second one or more of the corresponding plurality of transmission parameters;
receiving return pre-treatment signals at the plurality of receive transducers; and
determining the treatment characteristic based at least in part on the received return pre-treatment signals;
wherein the treatment characteristic is a treatment focus location of the proposed ultrasound treatment and wherein the method further comprises:
determining a plurality of receive focus profiles $\phi_{x,v_i}$;
each receive focus profile $\phi_{x,v_i}$ corresponding to a candidate treatment focus location x from among a plurality of X candidate locations and corresponding to an assumed ultrasound propagation velocity profile $v_i$ from among a plurality of I of assumed ultrasound propagation velocity profiles, and
each receive focus profile $\phi_{x,v_i}$ comprising N elements $\phi_{x,v_i}^n$, where N corresponds to a number of the plurality of receive transducers and the element $\phi_{x,v_i}^n$ comprises a phase offset or a time offset for an $n^{th}$ one of the plurality of receive transducers; and
wherein determining the plurality of receive focus profiles $\phi_{x,v_i}$ comprises, for each of the plurality of receive focus profiles $\phi_{x,v_i}$, determining the phase offset or the time offset for each element $\phi_{x,v_i}^n$ based on the candidate treatment focus location x, a location of the $n^{th}$ receive transducer relative to the treatment focus location x and the assumed velocity profile $v_i$; and
wherein determining the treatment characteristic based at least in part on the received return pre-treatment signals comprises determining the treatment focus location based at least in part on the received return pre-treatment signals and the receive focus profiles $\phi_{x,v_i}$;
wherein determining the phase offset or time offset for each element $\phi_{x,v_i}^n$ is based on:
an aligned model which specifies a physical and acoustic model of the head of the patient to be treated by the ultrasound therapy system; and
alignment between the model and at least one of: an estimated position of the $n^{th}$ receive transducer, and an estimated position of a structure which supports the receive transducers relative to the head of the patient;
wherein determining the phase offset or time offset for each element $\phi_{x,v_i}^n$ comprises:
selecting one (n*) of the plurality of receive transducers to be a reference transducer; and
for each element $\phi_{x,v_i}^n$ corresponding to an $n^{th}$ one of the plurality of receive transducers:

determining a phase or time $\psi_{x,v_i}{}^n$ of an ultrasound wave that would be received at the $n^{th}$ one of the plurality of receive transducers with the velocity profile $v_i$ from the candidate treatment focus location x based on a simulation of ultrasound propagation between the candidate treatment focus location x and the $n^{th}$ one of the plurality of receive transducers based on the velocity profile $v_i$; and determining $\phi_{x,v_i}{}^n$ be a phase offset or time offset between the determined phase or time $\psi_{x,v_i}{}^n$ for the $n^{th}$ one of the plurality of receive transducers and the determined phase or time $\psi_{x,v_i}{}^{n*}$ of the reference transducer according to $\phi_{x,v_i}{}^n = \psi_{x,v_i}{}^n - \psi_{x,v_i}{}^{n*}$).

2. The method of claim 1 comprising:
at least one of: injecting microbubbles into the patient before transmitting pre-treatment ultrasound energy into the brain of the patient, and injecting microbubbles into the patient during at least a portion of transmitting pre-treatment ultrasound energy into the brain of the patient; and
filtering the return pre-treatment signals to extract filtered return signals, each filtered return signal corresponding to one of the plurality of receive transducers and wherein determining the treatment characteristic based at least in part on the received return pre-treatment signals comprises determining the treatment characteristic based at least in part on the filtered return signals;
wherein the second one or more of the corresponding plurality of transmission parameters comprises a treatment frequency of the ultrasound transmission by the transmit transducer; and
wherein filtering the return pre-treatment signals to extract filtered return signals comprises band-pass filtering the return pre-treatment signals to extract, as the filtered return signals, a $2^{nd}$ or higher order harmonic of the treatment frequency.

3. The method of claim 1 wherein determining the treatment focus location based at least in part on the received return pre-treatment signals and the receive focus profiles $\phi_{x,v_i}$ comprises:
filtering the received return pre-treatment signals to extract filtered return signals, each filtered return signal corresponding to one of the receive transducers; and
determining the treatment focus location based at least in part on the filtered return signals and the receive focus profiles $\phi_{x,v_i}$.

4. The method of claim 3 wherein:
the second one or more of the corresponding plurality of transmission parameters comprises a treatment frequency of the ultrasound transmission by the transmit transducer;
filtering the received return pre-treatment signals to extract filtered return signals comprises filtering the received return pre-treatment signals using band pass filters; and
the band-pass filters are configured to extract, as the filtered return signals, one of: a fundamental (first harmonic) of the treatment frequency, and a $2^{nd}$ or higher order harmonic of the treatment frequency.

5. The method of claim 4 wherein:
the method comprises at least one of: injecting microbubbles into the patient before transmitting pre-treatment ultrasound energy into the brain of the patient, and during at least a portion of transmitting pre-treatment ultrasound energy into the brain of the patient;

the band-pass filters are configured to extract, as the filtered return signals, a $2^{nd}$ or higher order harmonic of the treatment frequency.

6. The method of claim 3 wherein determining the treatment focus location based at least in part on the filtered return signals and the receive focus profiles $\phi_{x,v_i}$ comprises:
for each receive focus profile $\phi_{x,v_i}$: applying the receive focus profile $\phi_{x,v_i}$ filtered return signals to determine phase-adjusted signals or time-adjusted signals, and summing the phase-adjusted signals or time-adjusted signals to determine a sum signal $S_{x,v_i}$ responding to the receive focus profile $\phi_{x,v_i}$; and
determining the focus location based at least in part on the sum signals $S_{x,v_i}$ corresponding to the plurality of receive focus profiles $\phi_{x,v_i}$.

7. The method of claim 6 wherein applying the receive focus profile $\phi_{x,v_i}$ to the filtered return signals to determine phase-adjusted signals or time-adjusted signals comprises, for each filtered return signal:
adjusting a phase of the filtered return signal by the phase offset of a corresponding element $\phi_{x,v_i}{}^n$ of the receive focus profile $\phi_{x,v_i}$ to thereby determine a corresponding phase-adjusted signal; or
adjusting a time of the filtered return signal by the time offset of a corresponding element $\phi_{x,v_i}{}^n$ of the receive focus profile $\phi_{x,v_i}$ to thereby determine a corresponding time-adjusted signal.

8. The method of claim 6 wherein determining the treatment focus location based at least in part on the sum signals $S_{x,v_i}$ corresponding to the plurality of receive focus profiles $\phi_{x,v_i}$ comprises: extracting a value $S_{x,v_i}{}^1$ from each sum signal $S_{x,v_i}$; and determining the treatment focus location based on the extracted values $S_{x,v_i}{}^1$.

9. The method of claim 3 wherein determining the treatment focus location based at least in part on the filtered return signals and the receive focus profiles $\phi_{x,v_i}$ comprises:
cross-correlating each of the filtered return signals with a reference one of the filtered return signals or another one of the filtered return signals to obtain a return phase offset or time offset profile $\gamma$, where the return phase offset or time offset profile $\gamma$ comprises one cross-correlation parameter $\gamma_n$ for each of the plurality of receive transducers, the cross-correlation parameter $\gamma_n$ indicative of a phase offset or time offset of the $n^{th}$ filtered return signal relative to the reference filtered return signal; and
determining the treatment focus location based at least in part on the return phase offset or time offset profile $\gamma$ and the plurality of receive focus profiles $\phi_{x,v_i}$.

10. The method of claim 9 wherein the reference one of the filtered return signals used to obtain the return phase offset or time offset profile $\gamma$ corresponds to the filtered return signal from a reference one of the plurality of receive transducers used for determining the receive focus profile $\phi_{x,v_i}$.

11. The method of claim 9 wherein determining the treatment focus location based at least in part on the return phase offset or time offset profile $\gamma$ and the plurality of receive focus profiles $\phi_{x,v_i}$ comprises: for each receive focus profile $\phi_{x,v_i}$, comparing the return phase offset or time offset profile $\gamma$ to the focus profile $\phi_{x,v_i}$ to obtain a corresponding similarity metric as between the return phase offset or time offset profile $\gamma$ and the receive focus profile $\phi_{x,v_i}$; and determining the focus location based on the similarity metrics for the plurality of receive focus profiles $\phi_{x,v_i}$.

12. The method of claim 1 comprising graphically displaying the determined treatment focus location in an image of the brain of the patient.

13. The method of claim 1 comprising:
confirming the determined treatment characteristic to be within a threshold similarity metric of the treatment characteristic, and
delivering ultrasound according to the proposed ultrasound treatment to open a blood brain barrier of the patient.

14. An ultrasound therapy system comprising:
a plurality of transmit transducers for transmitting ultrasound energy into the brain of a patient;
a plurality of receive transducers for receiving reflected ultrasound energy from the brain of the patient; and
a controller, the controller configured to:
obtain a proposed ultrasound treatment parameterized by, for each of the plurality of transmit transducers, treatment values for a corresponding plurality of transmission parameters;
cause the transmit transducers to transmit pre-treatment ultrasound energy into the brain of the patient, wherein transmitting the pre-treatment ultrasound energy comprises causing each of the plurality of transmit transducers to transmit ultrasound energy according to pre-treatment values for the corresponding plurality of transmission parameters, wherein:
the pre-treatment value for a transmission power is different than the treatment value for the transmission power, and
the pre-treatment values for a second one or more of the corresponding plurality of transmission parameters are the same as the treatment values for the second one or more of the corresponding plurality of transmission parameters;
receive return pre-treatment signals received at the plurality of receive transducers; and
determine the treatment characteristic based at least in part on the received return pre-treatment signals;
wherein the treatment characteristic is a treatment focus location of the proposed ultrasound treatment and wherein the controller is further configured to:
determine a plurality of receive focus profiles $\phi_{x,v_i}$;
each receive focus profile $\phi_{x,v_i}$ corresponding to a candidate treatment focus location x from among a plurality of X candidate locations and corresponding to an assumed ultrasound propagation velocity profile $v_i$ from among a plurality of I of assumed ultrasound propagation velocity profiles, and
each receive focus profile $\phi_{x,v_i}$ comprising N elements $\phi_{x,v_i}^n$, where N corresponds to a number of the plurality of receive transducers and the element $\phi_{x,v_i}^n$ comprises a phase offset or a time offset for an $n^{th}$ one of the plurality of receive transducers; and
wherein the controller is configured to determine the plurality of receive focus profiles $\phi_{x,v_i}$ by, for each of the plurality of receive focus profiles $\phi_{x,v_i}$, determining the phase offset or the time offset for each element $\phi_{x,v_i}^n$ based on the candidate treatment focus location x, a location of the $n^{th}$ receive transducer relative to the treatment focus location x and the assumed velocity profile $v_i$; and
wherein the controller is configured to determine the treatment characteristic based at least in part on the received return pre-treatment signals by determining the treatment focus location based at least in part on the received return pre-treatment signals and the receive focus profiles $\phi_{x,v_i}$;
wherein the controller is configured to determine the phase offset or time offset for each element $\phi_{x,v_i}^n$ based on:
an aligned model which specifies a physical and acoustic model of the head of the patient to be treated by the ultrasound therapy system; and
alignment between the model and at least one of: an estimated position of the $n^{th}$ receive transducer, and an estimated position of a structure which supports the receive transducers relative to the head of the patient;
wherein the controller is configured to determine the phase offset or time offset for each element $\phi_{x,v_i}^n$;
selecting one (n*) of the plurality of receive transducers to be a reference transducer; and
for each element $\phi_{x,v_i}^n$ corresponding to an $n^{th}$ one of the plurality of receive transducers:
determining a phase or time $\psi_{x,v_i}^n$ of an ultrasound wave that would be received at the $n^{th}$ one of the plurality of receive transducers with the velocity profile $v_i$ from the candidate treatment focus location x based on a simulation of ultrasound propagation between the candidate treatment focus location x and the $n^{th}$ one of the plurality of receive transducers based on the velocity profile $v_i$; and
determining $\phi_{x,v_i}^n$ to be a phase offset or time offset between the determined phase or time $\psi_{x,v_i}^n$ for the $n^{th}$ one of the plurality of receive transducers and the determined phase or time $\psi_{x,v_i}^{n*}$ the reference transducer according to $\phi_{x,v_i}^n = \psi_{x,v_i}^n - \psi_{x,v_i}^{n*}$).

15. The system of claim 14 wherein the system further comprises a microbubble injector for injecting microbubbles into the patient and wherein the controller is configured to:
cause the microbubble injector to at least one of: inject microbubbles into the patient before transmitting pre-treatment ultrasound energy into the brain of the patient, and inject microbubbles into the patient during at least a portion of transmitting pre-treatment ultrasound energy into the brain of the patient; and
filter the return pre-treatment signals to extract filtered return signals, each filtered return signal corresponding to one of the plurality of receive transducers and wherein the controller is further configured to determine the treatment characteristic based at least in part on the received return pre-treatment signals by determining the treatment characteristic based at least in part on the filtered return signals;
wherein the second one or more of the corresponding plurality of transmission parameters comprises a treatment frequency of the ultrasound transmission by the transmit transducer; and
wherein the controller is configured to filter the return pre-treatment signals to extract filtered return signals by band-pass filtering the return pre-treatment signals to extract, as the filtered return signals, a $2^{nd}$ or higher order harmonic of the treatment frequency.

16. The system of claim 14 wherein the controller is configured to determine the treatment focus location based at least in part on the received return pre-treatment signals and the receive focus profiles $\phi_{x,v_i}$ by:
filtering the received return pre-treatment signals to extract filtered return signals, each filtered return signal corresponding to one of the receive transducers; and determining the treatment focus location based at least in part on the filtered return signals and the receive focus profiles $\phi_{x,v_i}$.

17. The system of claim 16 wherein the controller is configured to determine the treatment focus location based at least in part on the filtered return signals and the receive focus profiles $\phi_{x,v_i}$ by:
for each receive focus profile $\phi_{x,v_i}$: applying the receive focus profile $\phi_{x,v_i}$ to the filtered return signals to determine phase-adjusted signals or time-adjusted signals, and summing the phase-adjusted signals or time-adjusted signals to determine a sum signal $S_{x,v_i}$ corresponding to the receive focus profile $\phi_{x,v_i}$; and
determining the focus location based at least in part on the sum signals $S_{x,v_i}$ corresponding to the plurality of receive focus profiles $\phi_{x,v_i}$.

18. The system of claim 17 wherein the controller is configured to determine the treatment focus location based at least in part on the sum signals $S_{x,v_i}$ corresponding to the plurality of receive focus profiles $\phi_{x,v_i}$ by: extracting a value $S_{x,v_i}^1$ from each sum signal $S_{x,v_i}$; and determining the treatment focus location based on the extracted values $S_{x,v_i}^1$.

19. The system of claim 16 wherein the controller is configured to determine the treatment focus location based at least in part on the filtered return signals and the receive focus profiles $\phi_{x,v_i}$ by:

cross-correlating each of the filtered return signals with a reference one of the filtered return signals or another one of the filtered return signals to obtain a return phase offset or time offset profile $\gamma$, where the return phase offset or time offset profile $\gamma$ comprises one cross-correlation parameter $\gamma_n$ for each of the plurality of receive transducers, the cross-correlation parameter $\gamma_n$ indicative of a phase offset or time offset of the $n^{th}$ filtered return signal relative to the reference filtered return signal; and determining the treatment focus location based at least in part on the return phase offset or time offset profile $\gamma$ and the plurality of receive focus profiles $\phi_{x,v_i}$.

20. The system of claim 14 wherein the controller is further configured to:
confirm the determined treatment characteristic to be within a threshold similarity metric of the treatment characteristic, and
cause the plurality of transmit transducers to deliver ultrasound according to the proposed ultrasound treatment to open a blood brain barrier of the patient.

* * * * *